United States Patent
Wiley

(10) Patent No.: US 7,517,962 B2
(45) Date of Patent: Apr. 14, 2009

(54) TWEAK RECEPTOR

(75) Inventor: Steven R. Wiley, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 145 days.

(21) Appl. No.: 10/862,109

(22) Filed: Jun. 4, 2004

(65) Prior Publication Data

US 2006/0084143 A1 Apr. 20, 2006

Related U.S. Application Data

(60) Continuation of application No. 10/754,847, filed on Jan. 8, 2004, which is a division of application No. 09/883,777, filed on Jun. 18, 2001, now Pat. No. 6,727,225, which is a continuation-in-part of application No. PCT/US00/34755, filed on Dec. 19, 2000, and a continuation-in-part of application No. 09/742,454, filed on Dec. 19, 2000, now Pat. No. 6,824,773.

(60) Provisional application No. 60/172,878, filed on Dec. 20, 1999, provisional application No. 60/203,347, filed on May 10, 2000.

(51) Int. Cl.
*C07K 16/00* (2006.01)
*C12N 5/12* (2006.01)
*A61K 39/395* (2006.01)

(52) U.S. Cl. .............. 530/387.1; 424/130.1; 424/178.1; 435/326

(58) Field of Classification Search ........................ None
See application file for complete search history.

(56) References Cited

U.S. PATENT DOCUMENTS

2003/0105297 A1  6/2003  Ruben et al.

FOREIGN PATENT DOCUMENTS

| WO | WO 98/55508 | * 12/1998 |
| WO | WO 99/61471 | * 12/1999 |
| WO | WO 01/45730 | 6/2001 |
| WO | WO 02/22166 | 3/2002 |

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Nakayama M., et al. "Fibroblast growth factor—inducible 14 mediates multiple pathways of TWEAK-induced cell death," *J. Immunol* 170(1): 341-348, 2003.
Nakayama M., et al. "Characterization of murine TWEAK and its receptor (Fn14) by monoclonal antibodies," *Biocheml Biophys Resh Communis*, 306: 819-825, 2003.
Wiley et al., "TWEAK, a member of the TNF superfamily, is a multifunctional cytokine that binds the TweakR/Fn14 receptor," *Cytokine And Growth Factor Reviews*, 14: 241-249, 2003.
PCT/US2005/037582 International Search Report.

* cited by examiner

*Primary Examiner*—Christopher H Yaen
(74) *Attorney, Agent, or Firm*—Nathan A. Machin

(57) ABSTRACT

The present invention provides the TWEAK receptor and methods for identifying and using agonists and antagonists of the TWEAK receptor. In particular, the invention provides methods of screening for agonists and antagonists and for treating diseases or conditions mediated by angiogenesis, such as solid tumors and vascular deficiencies of cardiac or peripheral tissue.

37 Claims, 9 Drawing Sheets

```
  1 MAPGWPRSLPQILVLGFGLVLMRAAAGEQAPGTSPCSSGSSWSADLDKCM 50
    ||| || .:|||   | |:|. |||||||.||| |||||||||||||||
  1 MARGSLRRLLRLLVLGLWLALLRSVAGEQAPGTAPCSRGSSWSADLDKCM 50

51 DCASCPARPHSDFCLGCAAAPPAHFRLLWPILGGALSLVLVLALVSSFLV 100
    |||| |||||||||||||||||| |||||||||||||| ||.| ||||||
 51 DCASCRARPHSDFCLGCAAAPPAPFRLLWPILGGALSLTFVLGLLSGFLV 100

101 WRRCRRREKFTTPIEETGGEGCPGVALIQ 129
    |||||||||||||||||||||||| ||||
101 WRRCRRREKFTTPIEETGGEGCPAVALIQ 129
```

FIG. 1A

MARGSLRRLL RLLVLGLWLA LLRSVAGEQA
PGTAPCSRGS SWSADLDKCM DCASCRARPH
SDFCLGCAAA PPAPFRLLWP ILGGALSLTF
VLGLLSGFLV WRRCRRREKF TTPIEETGGE
GCPAVALIQ

Leader Cysteine [Transmembrane]

*Fig. 1B*

TWEAK RECEPTOR

REFERENCE TO RELATED APPLICATIONS

This application is a continuation of U.S. patent application Ser. No. 10/754,847, filed Jan. 8, 2004, which is a divisional of U.S. patent application Ser. No. 09/883,777, filed Jun. 18, 2001, now U.S. Pat. No. 6,727,225 which is a continuation-in-part of International Application No. PCT/US00/34755, filed 19 Dec. 2000, and is a continuation-in-part of U.S. patent application Ser. No. 09/742,454, filed Dec. 19, 2000, now U.S. Pat. No. 6,824,773 both of which claim the benefit of U.S. Provisional Application Ser. No. 60/172,878, filed 20 Dec. 1999, and U.S. Provisional Application Ser. No. 60/203,347, filed 10 May 2000. The above-identified applications are incorporated herein by reference.

FIELD OF THE INVENTION

The present invention relates to the discovery of the functional TWEAK receptor (TWEAKR) for the TWEAK protein. More particularly, the invention relates to the use of TWEAKR agonists and antagonists in methods of treatment, and to screening methods based on TWEAKR and the TWEAK-TWEAKR interaction.

BACKGROUND

Angiogenesis is a multi-step developmental process that results in the formation of new blood vessels off of existing vessels. This spatially and temporally regulated process involves loosening of matrix contacts and support cell interactions in the existing vessels by proteases, followed by coordinated movement, morphological alteration, and proliferation of the smooth muscle and endothelial cells of the existing vessel. The nascent cells then extend into the target tissue followed by cell-cell interactions in which the endothelial cells form tubes which the smooth muscle cells surround. In a coordinated fashion, extracellular matrix proteins of the vessel are secreted and peri-endothelial support cells are recruited to support and maintain structural integrity (see, e.g., Daniel et al., Ann. Rev. Physiol. 2000(62):649, 2000). Angiogenesis plays important roles in both normal and pathological physiology.

Under normal physiological conditions, angiogenesis is involved in fetal and embryonic development, wound healing, organ regeneration, and female reproductive remodeling processes including formation of the endometrium, corpus luteum, and placenta. Angiogenesis is stringently regulated under normal conditions, especially in adult animals, and perturbation of the regulatory controls can lead to pathological angiogenesis.

Pathological angiogenesis has been implicated in the manifestation and/or progression of inflammatory diseases, certain eye disorders, and cancer. In particular, several lines of evidence support the concept that angiogenesis is essential for the growth and persistence of solid tumors and their metastases (see, e.g., Folkman, N. Engl. J. Med. 285:1182, 1971; Folkman et al., Nature 339:58, 1989; Kim et al., Nature 362:841, 1993; Hori et al., Cancer Res., 51:6180, 1991). Angiogenesis inhibitors are therefore useful for the prevention (e.g., treatment of premalignant conditions), intervention (e.g., treatment of small tumors), and regression (e.g., treatment of large tumors) of cancers (see, e.g., Bergers et al., Science 284:808, 1999).

The TWEAK protein, which has also been called TREPA and Apo3L, is a member of the tumor necrosis factor (TNF) family and is expressed in a wide variety of human tissues (Chicheportiche et al., J. Biol. Chem., 272(51):32401, 1997; see also Wiley, PCT Publication No. WO 98/35061, 13 Aug. 1998). Like most TNF family members, TWEAK is a Type II membrane protein with an extracellular C-terminal domain. Although TWEAK was originally described as a weak inducer of apoptosis, this induction of cell death was later shown to be indirect (Schneider et al., Eur. J. Immunol. 29:1785, 1999).

Lynch et al. demonstrated that TWEAK directly induces endothelial cell proliferation and angiogenesis (J. Biol. Chem., 274(13):8455, 1999). Picomolar concentrations of recombinant soluble TWEAK induce proliferation in multiple endothelial cell lines and in aortic smooth muscle cells, and reduce the requirement for serum and growth factors in culture. Moreover, TWEAK induces a strong angiogenic response in a rat corneal pocket assay. Since TNF family members initiate biological responses by signaling through members of the TNF receptor family, there has been great interest in identifying and characterizing a TWEAKR.

Marsters et al. reported that TWEAK binds to and signals through a death-domain containing receptor known variously as DR3, Apo3, WSL-1, TRAMP, or LARD (Marsters et al., Current Biology 8(9):525, 1998). Schneider et al., however, showed that TWEAK binds to and signals in Kym-1 cells but that Kym-1 cells do not express the receptor DR3 (Schneider et al., Eur. J. Immunol. 29:1785, 1999). These results suggest the existence of a yet to be identified TWEAK receptor.

Because TWEAK induces angiogenesis ill vivo, there is a particular need to identify the major functional TWEAKR. Once identified, TWEAKR may be used to screen for and develop TWEAKR agonists and antagonists for the modulation of angiogenesis and the treatment of human disease.

There is a need for additional compositions and methods of modulating angiogenesis for the prevention, abrogation, and mitigation of disease.

SUMMARY OF THE INVENTION

The present invention is based upon the identification and biological characterization of the major functional TWEAK receptor (TWEAKR). As described below, cDNA encoding the TWEAKR was molecularly cloned from a human endothelial cell expression library.

Although DNA and deduced amino acid sequences corresponding to the TWEAKR identified herein have been reported (see, e.g., Kato et al., PCT Publication No. WO 98/55508, 10 Dec. 1998 and Incyte, PCT Publication No. WO 99/61471, 02 Dec. 1999), it was not heretofore appreciated that these sequences encode a receptor for TWEAK or that the encoded polypeptide, fragments, agonsits, or antagonists thereof can be used to modulating angiogenesis. Similarly, investigators have recently claimed methods of making and using TWEAKR antagonists to treat immunological disorders, but without identifying the major TWEAKR or its role in angiogenesis (Rennert, PCT Publication No. WO 00/42073, 20 Jul. 2000). These deficiencies have been addressed, as described herein, by identification of the major TWEAKR and characterization of its biological activities. The identification of TWEAKR has led to the development of compositions for the modulation of angiogenesis, and also provides screening tools for the identification of diagnostics and therapeutics.

The invention provides a method of modulating angiogenesis in a subject in need of such treatment comprising administering a therapeutically-effective amount of a composition comprising a TWEAKR, a TWEAKR antagonist, or a TWEAKR agonist. The subject is a mammal, preferably a human. A composition useful in the methods of the invention comprises a TWEAKR polypeptide having a sequence as set forth in SEQ ID NO:4, including fragments and variants thereof. In one embodiment, the composition comprises a sequence of amino acids from about residue 28 to an amino acid residue from about 68-80 of SEQ ID NO:4. In one embodiment angiogenesis is inhibited. A TWEAKR antagonist includes, for example, a soluble TWEAKR fragment; an anti-TWEAKR antibody; an antisense or triple helix forming nucleic acid that binds to a TWEAK or TWEAKR nucleic acid molecule; peptides; and small molecules. In another embodiment, the TWEAKR antagonist comprises the extracellular domain of TWEAKR, or fragment thereof, and an Fc or leucine zipper domain.

The invention also provides a method of modulating the interaction of TWEAK and TWEAKR. The method includes contacting a cell comprising TWEAK or TWEAKR with a composition comprising an agent selected from the group consisting of: (a) a soluble TWEAKR extracellular domain, and (b) an antibody that binds to the TWEAKR extracellular domain, under conditions such that the cell and the composition interact. The contacting may be in vitro, ex vivo, or in vivo.

The invention further provides a method for targeting a detectable label or chemotherapeutic to a vascular tissue comprising contacting the vascular tissue with an antibody that binds TWEAKR.

In yet another aspect the invention provides a purified polypeptide consisting of amino acid 28 to $x_1$ of SEQ ID NO:4, wherein $x_1$ is an amino acid from about 68 to 80 of SEQ ID NO:4 and naturally occurring variants thereof.

Also provided by the invention is a fusion polypeptide comprising a polypeptide consisting of amino acid 28 to $x_1$ of SEQ ID NO:4, wherein $x_1$ is an amino acid from about 68 to 80 of SEQ ID NO:4 and naturally occurring variants thereof, operably linked to a polypeptide of interest. The polypeptide of interest can be any series of amino acids and includes an Fc polypeptide, leucine zipper polypeptide, or an peptide linker. In one embodiment the fusion polypeptide has a sequence as set forth in SEQ ID NO: 7 or 9.

The invention also provides an isolated polypeptide comprising a sequence $Z_1$-X-$Z_2$, wherein $Z_1$, and $Z_2$ are each individually a polypeptide consisting of amino acid 28 to $x_1$ of SEQ ID NO:4, wherein $x_1$ is an amino acid from about 68 to 80 of SEQ ID NO:4 and naturally occurring variants thereof, and X is a peptide linker. In one embodiment $Z_1$, and $Z_2$ have the same amino acid sequence. In another embodiment $Z_1$, and $Z_2$ have different amino acid sequences. The X moiety can be any peptide linker including, for example, --Gly-Gly--, GGGGS (SEQ ID NO:10) (GGGGS)$_n$ (SEQ ID NO: 11), GKSSGSGSESKS (SEQ ID NO:12), GSTSGSGKSSEGKG (SEQ ID NO:13), GSTSGSGKSSEGSGSTKG (SEQ ID NO:14), GSTSGSGKPGSGEGSTKG (SEQ ID NO:15), and EGKSSGSGSESKEF (SEQ ID NO:16). In another embodiment, the polypeptide comprises $Z_1$-X-$Z_2$(-X-Z)$_n$, wherein 'n' is any integer, but is preferably 1 or 2.

The invention further provides an isolated polynucleotide encoding the purified polypeptide consisting of amino acid 28 to $x_1$ of SEQ ID NO:4, wherein $x_1$, is an amino acid from about 68 to 80 of SEQ ID NO:4 and naturally occurring variants thereof. In one embodiment, the polynucleotide as a sequence of nucleotides from about 134 to $x_2$ of SEQ ID NO:3, wherein $x_2$ is a nucleotide from about 256 to 292 of SEQ ID NO:3.

The invention provides an isolated polynucleotide encoding a fusion polypeptide of the invention. In one embodiment, the polynucleotide has a sequence of nucleotides from about 134 to $x_2$ of SEQ ID NO:3, wherein $x_2$ is a nucleotide from about 256 to 292 of SEQ ID NO:3. In another aspect, the polynucleotide has a sequence as set forth in SEQ ID NO:6 or 8.

The invention includes vectors comprising the polynucleotide of the invention as well as host cells comprising a polynucleotide of the invention. The host cell can be an animal cell, a plant cell, and a bacterial cell (e.g., *E. coli, Bacillus subtilis*, and *Salmonella typhimurium*).

BRIEF DESCRIPTION OF THE DRAWINGS

FIG. 1A shows a sequence alignment of the human and murine TWEAKR polypeptide sequences. The top sequence is the murine TWEAKR polypeptide (SEQ ID NO:5), and the bottom sequence is the human TWEAKR polypeptide (SEQ ID NO:4).

FIG. 1B shows the primary amino acid sequence of TweakR showing major features. The leader sequence in underlined. The arrow indicates the predicted site of cleavage of the leader sequence. The region of TNF family receptor homology is shown in bold. The predicted transmembrane region is doubly underlined. The putative c TRAF binding motif in the cytoplasmic domain is boxed.

DETAILED DESCRIPTION OF THE INVENTION

Figure 2:
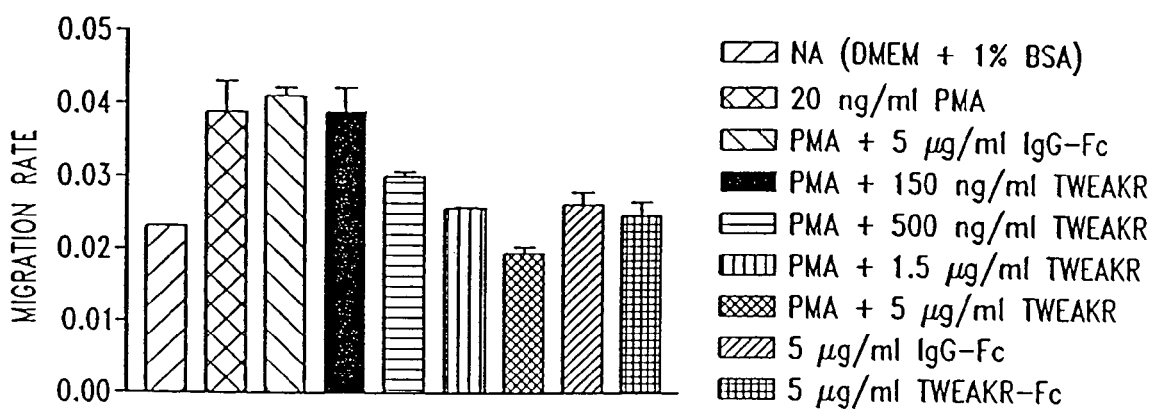
FIG. 2 shows the effect of TWEAKR-Fc on PMA-induced HRMEC wound closure.

The present invention is directed to TWEAKR and methods for identifying and using agonists and antagonists of TWEAKR. The invention provides methods of screening for agonists and antagonists and for treating diseases or conditions mediated by angiogenesis.

Abbreviations and Terminology Used in the Specification

"4-1BB" and "4-1BB ligand" (4-1BB-L) are polypeptides described, inter alia, in U.S. Pat. No. 5,674,704, including soluble forms thereof.

"CD40 ligand" (CD40L) is a polypeptide described, inter alia, in U.S. Pat. No. 5,716,805, including soluble forms thereof.

"Flt3L" is Flt3 ligand, a polypeptide described, inter alia, in U.S. Pat. No. 5,554,512, including soluble forms thereof.

"RTKs" are receptor tyrosine kinases.

"Tek," which has also been called Tie2 and ork, is an RTK that is predominantly expressed in vascular endothelium. The molecular cloning of human Tek (ork) has been described by Ziegler, U.S. Pat. No. 5,447,860. "Tek antagonists" are described, inter alia, in Cerretti et al., PCT Publication No. WO 00/75323, 14 Dec. 2000.

"TRAIL" is TNF-related apoptosis-inducing ligand, a type II transmembrane polypeptide in the TNF family described, inter alia, in U.S. Pat. No. 5,763,223, including soluble forms thereof.

"VEGF" is vascular endothelial growth factor, also known as VPF or vascular permeability factor.

Soluble TWEAKR Polypeptides

As described in the examples below, the native human TWEAKR cDNA has a sequence as set forth in SEQ ID NO:3, which encodes a 129 residue polypeptide (SEQ ID NO:4). Several distinct regions can be discerned within the TWEAKR polypeptides of the invention (see, e.g., FIG. 1). A leader sequence, also called a signal peptide, is present in these polypeptides. The leader sequence present in the full-length TWEAKR polypeptide of the invention is predicted to include amino acids 1-27 of SEQ ID NO:4. The signal peptide cleavage site for TWEAKR polypeptide can be predicted using a computer algorithm. However, one of skill in the art will recognize that the cleavage site of the signal sequence may vary depending upon a number of factors including the organism in which the polypeptide is expressed. Accordingly, the N-terminus of a mature form of a TWEAKR polypeptide of the invention may vary by about 2 to 5 amino acids. Thus, a mature form of a TWEAKR polypeptide of the invention may include at its N-terminus amino acid 22, 23, 24, 25, 26, 27, 28, 29, 30, 31, or 32 of SEQ ID NO:4. Accordingly, a mature form of a TWEAKR polypeptide includes amino acids 23, 24, 25, 26, 27, 28, 29, 30, 31, 32 or 33 to about amino acid 129 (or, in the case of a soluble polypeptide, an amino acid between 68 and 80) of SEQ ID NO:4. The extracellular region of a TWEAKR polypeptide is located at about amino acids 28 to 80 of SEQ ID NO:4. The transmembrane region for the TWEAKR polypeptide is located at about amino acids 81 to 100 of SEQ ID NO:4. The intracellular region is located at about amino acids 101 to 129 of SEQ ID NO:4. A putative TWEAKR sequence has also been reported by Kato et al., PCT Publication No. WO 98/55508, 10 Dec. 1998 and by Incyte, PCT Publication No. WO 99/61471, 2 Dec. 1999. As used herein, "TWEAKR" includes polypeptides having these sequences, and in particular comprising amino acids 28 to $x_1$ of SEQ ID NO:4, wherein $x_1$ is an amino acid from 68 to 80 of SEQ ID NO:4, as well as naturally occurring variants thereof.

The invention provides both full-length and mature forms of TWEAKR polypeptides. Full-length polypeptides are those having the complete primary amino acid sequence of the polypeptide as initially translated (see, e.g., SEQ ID NO:4). The amino acid sequences of full-length polypeptides can be obtained, for example, by translation of the complete open reading frame ("ORF") of a cDNA molecule (see, e.g., SEQ ID NO:3). An example of a full length TWEAKR polypeptide of the invention comprises a sequence as set forth in SEQ ID NO:4 from amino acid 1 to amino acid 129. Such a full length polypeptide is contemplated to include, for example, the signal peptide comprising amino acid I to about amino acid 27 of SEQ ID NO:4.

The "mature form" of a polypeptide refers to a polypeptide that has undergone post-translational processing steps, if any, such as, for example, cleavage of the signal sequence or proteolytic cleavage to remove a prodomain. Multiple mature forms of a particular full-length polypeptide may be produced, for example, by imprecise cleavage of the signal sequence, or by differential regulation of proteases that cleave the polypeptide. The mature form(s) of such polypeptide may be obtained by expression, in a suitable mammalian cell or other host cell, of a polynucleotide that encodes the full-length polypeptide. The sequence of the mature form of the polypeptide may also be determinable from the amino acid sequence of the full-length form, through identification of signal sequences or protease cleavage sites (e.g., a protease cleavage site is predicted between the Gly-Glu residues at positions 27 and 28 of SEQ ID NO:4). An example of a mature form of a TWEAKR polypeptide of the invention comprises a sequence as set forth in SEQ ID NO:4 from about amino acid 28 to amino acid 129.

In another aspect of the invention, fragments of TWEAKR polypeptides are provided. Such fragments include, for example, the various domains identified above (e.g., the signal sequence domain, the extracellular domain, the transmembrane domain, and the cytoplasmic or intracellular domain). Such domains find use in recombinant DNA techniques (e.g., creation of fusion proteins and the like). Of particular interest is the extracellular domain of TWEAKR from about amino acid 28 to amino acid 68 to 80 of SEQ ID NO:4. The extracellular domain of TWEAKR comprises a soluble TWEAKR amino acid sequence. Also included in the invention are fragments of the extracellular domain that retain a biological activity of TWEAKR. For example, a biological activity associated with a TWEAKR extracellular domain or fragment thereof includes the ability to bind to TWEAK.

In one aspect of the invention, a soluble TWEAKR fragment is used as a TWEAKR antagonist to inhibit angiogenesis and/or to inhibit the binding of TWEAK ligand to TWEAKR. A TWEAKR fragment preferably comprises the extracellular domain of TWEAKR or a portion thereof as described herein such that the fragment comprises a soluble TWEAKR amino acid sequence. Accordingly, a TWEAKR antagonist includes, for example, a soluble portion of the TWEAKR molecule, preferably a portion of the extracellular domain of TWEAKR, either alone, fused, or conjugated to one or more other molecules or polypeptides (e.g., an Fc, leucine zipper polypeptide, or a peptide linker). For example, the invention provides compositions and fusion proteins that comprise at least one soluble TWEAKR polypeptide domain (e.g., the extracellular domain).

Soluble polypeptides are capable of being secreted from the cells in which they are expressed. The use of soluble forms of polypeptides is advantageous for certain applications. Purification of the polypeptides from recombinant host cells is facilitated since the polypeptides are secreted, and soluble proteins are generally suited for parenteral administration. A secreted soluble polypeptide may be identified (and distinguished from its non-soluble membrane-bound counterparts) by separating intact cells which express the desired polypeptide from the culture medium, e.g., by centrifugation, and assaying the medium (supernatant) for the presence of the desired polypeptide. The presence of the desired polypeptide in the medium indicates that the polypeptide was secreted from the cells and thus is a soluble form of the polypeptide. Soluble polypeptides may be prepared by any of a number of conventional techniques. A polynucleotide encoding a desired soluble polypeptide may be subcloned into an expression vector for production of the polypeptide, or the desired encoding polynucleotide or soluble polypeptide may be chemically synthesized. Examples of a nucleic acid molecule encoding a soluble TWEAKR polypeptide comprises about nucleotides 134 to 256, 134 to 262, 134 to 289, and 134 to 292 of SEQ ID NO:3. In one embodiment, D-amino acids are substituted for the naturally occurring L-amino acids. D-amino acids provide improved stability under in vivo conditions. In addition, due to the size of the extracellular domain or soluble polypeptide sequence of the invention it may be advantageous to synthesize the polypeptide using D-amino acids. It will be recognized that the polypeptide of the invention can be synthesized such that the polypeptide comprises a combination of L- and D-amino acids.

Soluble TWEAKR polypeptides comprise all or part of the TWEAKR extracellular domain, but generally lack the transmembrane domain that would cause retention of the polypeptide at the cell surface. Soluble polypeptides may include part of the transmembrane domain or all or part of the cytoplasmic domain so long as the polypeptide is secreted from the cell in which it is produced. Soluble TWEAKR polypeptides advantageously comprise a native or heterologous signal peptide when initially synthesized, to promote secretion from the cell, but the signal sequence is cleaved upon secretion. The term "TWEAKR extracellular domain" is intended to encompass all or part of the native TWEAKR extracellular domain, as well as related forms including but not limited to: (a) fragments, (b) variants, (c) derivatives, and (d) fusion polypeptides. The ability of these related forms to inhibit angiogenesis or other TWEAKR-mediated responses may be determined in vitro or in vivo, using methods such as those exemplified below or using other assays known in the art. Examples of soluble TWEAKR polypeptides are provided below. In some embodiments of the present invention a multimeric form of a soluble TWEAKR polypeptide ("soluble TWEAKR multimer") is used as an antagonist to block the binding of TWEAK to TWEAKR, to inhibit angiogenesis or other TWEAKR-mediated responses.

Soluble TWEAKR multimers are covalently-linked or non-covalently-linked multimers, including dimers, trimers, or higher multimers. Multimers may be linked by disulfide bonds formed between cysteine residues on different soluble TWEAKR polypeptides. One embodiment of the invention is directed to multimers comprising multiple soluble TWEAKR polypeptides joined via covalent or non-covalent interactions between peptide moieties fused to the soluble TWEAKR polypeptides. Such peptides may be peptide linkers (spacers), or peptides that have the property of promoting multimerization. In one embodiment peptide linkers are fused to the C-terminal end of a first soluble TWEAKR molecule and the N-terminal end of a second soluble TWEAKR molecule. This structure may be repeated multiple times such that at least one, preferably 2, 3, 4, or more soluble TWEAKR polypeptides are linked to one another via peptide linkers at their respective termini. For example, a polypeptide of the invention comprises a sequence $Z_1$-X-$Z_2$, wherein $Z_1$, and $Z_2$ are each individually a polypeptide consisting of amino acid 28 to $x_1$, of SEQ ID NO:4, wherein $x_1$ is an amino acid from about 68 to 80 of SEQ ID NO:4 and X is a peptide linker. In another embodiment, the polypeptide comprises $Z_1$-X-$Z_2$(-X-Z)$_n$, wherein 'n' is any integer, but is preferably 1 or 2. In a further embodiment, the peptide linkers should be of sufficient length to allow the soluble TWEAKR polypeptide to form bonds with adjacent soluble TWEAKR polypeptides. Examples of peptide linkers include --Gly-Gly--, GGGGS (SEQ ID NO: 10) (GGGGS)$_n$ (SEQ ID NO: 11), GKSSGSGSESKS (SEQ ID NO:12), GSTSGSGKSSEGKG (SEQ ID NO: 13), GSTSGSGKSSEGSGSTKG (SEQ ID NO: 14), GSTSGS-GKPGSGEGSTKG (SEQ ID NO:15), or EGKSSGSG-SESKEF (SEQ ID NO:16). Linking moieties are described, for example, in Huston, J. S., et al., PNAS 85:5879-5883 (1988), Whitlow, M., et al., Protein Engineering 6:989-995 (1993), and Newton, D. L., et al., Biochemistry 35:545-553 (1996). Other suitable peptide linkers are those described in U.S. Pat. No. 4,751,180 and 4,935,233, which are hereby incorporated by reference. A polynucleotide encoding a desired peptide linker can be inserted between, and in the same reading frame as, a polynucleotide encoding a soluble TWEAKR polypeptide, using any suitable conventional technique. In particular embodiments, a fusion polypeptide comprises from two to four soluble TWEAKR polypeptides separated by peptide linkers.

In some embodiments, a soluble TWEAKR multimer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al. (Proc. Natl. Acad. Sci. USA 88:10535, 1991); Byrn et al. (Nature 344:677, 1990); and Hollenbaugh and Aruffo ("Construction of Immunoglobulin Fusion Proteins", in *Current Protocols in Immunology*, Suppl. 4, pages 10.19.1-10.19.11, 1992).

One preferred embodiment of the present invention is directed to a TWEAKR-Fc dimer comprising two fusion proteins created by fusing a soluble TWEAKR to an Fc polypeptide. A gene fusion encoding the TWEAKR-Fc fusion protein is inserted into an appropriate expression vector. TWEAKR-Fc fusion proteins are expressed in host cells transformed with the recombinant expression vector, and allowed to assemble much like antibody molecules, whereupon interchain disulfide bonds form between the Fc moieties to yield divalent soluble TWEAKR. The term "Fc polypeptide" as used herein includes native and mutein forms of polypeptides derived from the Fc region of an antibody. Truncated forms of such polypeptides containing the hinge region that promotes dimerization are also included.

One suitable Fc polypeptide, described in PCT application WO 93/10151, is a single chain polypeptide extending from the N-terminal hinge region to the native C-terminus of the Fc region of a human IgGI antibody. Another useful Fc polypeptide is the Fc mutein described in U.S. Pat. No. 5,457,035 and by Baum el al., EMBO J. 13:3992, 1994. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors. Fusion polypeptides comprising Fc moieties, and multimers formed therefrom, offer an advantage of facile purification by affinity chromatography over Protein A or Protein G columns, and Fc fusion polypeptides may provide a longer in vivo half life, which is useful in therapeutic applications, than unmodified polypeptides.

In other embodiments, a soluble TWEAKR polypeptide may be substituted for the variable portion of an antibody heavy or light chain. If fusion proteins are made with both heavy and light chains of an antibody, it is possible to form a soluble TWEAKR multimer with as many as four soluble TWEAKR polypeptides.

Another method for preparing soluble TWEAKR multimers involves use of a leucine zipper domain. Leucine zipper domains are peptides that promote multimerization of the proteins in which they are found. Leucine zippers were originally identified in several DNA-binding proteins (Landschulz et al., Science 240:1759, 1988), and have since been found in a variety of different proteins. Among the known leucine zippers are naturally occurring peptides and derivatives thereof that dimerize or trimerize. Examples of leucine zipper domains suitable for producing soluble multimeric proteins are described in PCT application WO 94/10308, and the leucine zipper derived from lung surfactant protein D (SPD) described in Hoppe et al. FEBS Lett. 344:191, 1994. The use of a modified leucine zipper that allows for stable trimerization of a heterologous protein fused thereto is described in Fanslow et al., Semin. Immunol. 6:267, 1994. Recombinant fusion proteins comprising a soluble TWEAKR polypeptide fused to a leucine zipper peptide are expressed in suitable host cells, and the soluble TWEAKR multimer that forms is recovered from the culture supernatant.

For some applications, the soluble TWEAKR multimers of the present invention are believed to provide certain advantages over the use of monomeric forms. Fc fusion polypeptides, for example, typically exhibit an increased in vivo half-life as compared to an unmodified polypeptide.

The present invention encompasses the use of various forms of soluble TWEAKR multimers that retain the ability to inhibit angiogenesis or other TWEAKR-mediated responses. The term "soluble TWEAKR multimer" is intended to encompass multimers containing all or part of the native TWEAKR extracellular domain, as well as related forms including, but not limited to, multimers of: (a) fragments, (b) variants, (c) derivatives, and (d) fusion polypeptides of soluble TWEAKR. The ability of these related forms to inhibit angiogenesis or other TWEAKR-mediated responses may be determined in vitro or in vivo, using methods such as those exemplified in the examples or using other assays known in the art.

Among the soluble TWEAKR polypeptides and soluble TWEAKR multimers useful in practicing the present invention are TWEAKR variants that retain the ability to bind ligand (e.g., TWEAK) and/or inhibit angiogenesis or other TWEAKR-mediated responses. Such TWEAKR variants include polypeptides that are substantially homologous to native TWEAKR, but which have an amino acid sequence different from that of a native TWEAKR because of one or more deletions, insertions or substitutions. Particular embodiments include, but are not limited to, TWEAKR polypeptides that comprise from one to ten deletions, insertions or substitutions of amino acid residues, when compared to a native TWEAKR sequence. Included as variants of TWEAKR polypeptides are those variants that are naturally occurring, such as allelic forms and alternatively spliced forms, as well as variants that have been constructed by modifying the amino acid sequence of a TWEAKR polypeptide or the nucleotide sequence of a nucleic acid encoding a TWEAKR polypeptide.

Generally, substitutions for one or more amino acids present in the native polypeptide should be made conservatively. Examples of conservative substitutions include substitution of amino acids outside of the active domain(s), and substitution of amino acids that do not alter the secondary and/or tertiary structure of TWEAKR. Additional examples include substituting one aliphatic residue for another, such as Ile, Val, Leu, or Ala for one another, or substitutions of one polar residue for another, such as between Lys and Arg; Glu and Asp; or Gln and Asn, or substitutions of one aromatic residue for another, such as Phe, Trp, or Tyr for one another. Other such conservative substitutions, for example, substitutions of entire regions having similar hydrophobicity characteristics, are known in the art.

In some preferred embodiments, the TWEAKR variant is at least about 70% identical in amino acid sequence to the amino acid sequence of native TWEAKR; in some preferred embodiments, the TWEAKR variant is at least about 80% identical in amino acid sequence to the amino acid sequence of native TWEAKR. In some more preferred embodiments, the TWEAKR variant is at least about 90% identical in amino acid sequence to the amino acid sequence of native TWEAKR; in some more preferred embodiments, the TWEAKR variant is at least about 95% identical in amino acid sequence to the amino acid sequence of native TWEAKR. In some most preferred embodiments, the TWEAKR variant is at least about 98% identical in amino acid sequence to the amino acid sequence of native TWEAKR; in some most preferred embodiments, the TWEAKR variant is at least about 99% identical in amino acid sequence to the amino acid sequence of native TWEAKR. Percent identity, in the case of both polypeptides and nucleic acids, may be determined by visual inspection. Percent identity may also be determined using the alignment method of Needleman and Wunsch (J. Mol. Biol. 48:443, 1970) as revised by Smith and Waterman (Adv. Appl. Math 2:482, 1981. Preferably, percent identity is determined by using a computer program, for example, the GAP computer program version 10.x available from the Genetics Computer Group (GCG; Madison, Wis., see also Devereux et al., *Nucl. Acids Res.* 12:387, 1984). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353-358, 1979 for amino acids; (2) a penalty of 30 (amino acids) or 50 (nucleotides) for each gap and an additional 1 (amino acids) or 3 (nucleotides) penalty for each symbol in each gap; (3) no penalty for end gaps; and (4) no maximum penalty for long gaps. Other programs used by one skilled in the art of sequence comparison may also be used. For fragments of TWEAKR, the percent identity is calculated based on that portion of TWEAKR that is present in the fragment.

The present invention further encompasses the use of soluble TWEAKR polypeptides with or without associated native-pattern glycosylation. TWEAKR expressed in yeast or mammalian expression systems (e.g., COS-1 or COS-7 cells) may be similar to or significantly different from a native TWEAKR polypeptide in molecular weight and glycosylation pattern, depending upon the choice of expression system. Expression of TWEAKR polypeptides in bacterial expression systems, such as *E. coli*, provides non-glycosylated molecules. Different host cells may also process polypeptides differentially, resulting in heterogeneous mixtures of polypeptides with variable N- or C-termini.

The primary amino acid structure of soluble TWEAKR polypeptides may be modified to create derivatives by forming covalent or aggregative conjugates with other chemical moieties, such as glycosyl groups, lipids, phosphate, acetyl groups and the like. Covalent derivatives of TWEAKR may be prepared by linking particular functional groups to TWEAKR amino acid side chains or at the N-terminus or C-terminus of a TWEAKR polypeptide. In addition, TWEAKR can be complexed with polyethylene glycol (PEG), metal ions, or incorporated into polymeric compounds such as polyacetic acid, polyglycolic acid, hydrogels, dextran, and the like, or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

Fusion polypeptides of soluble TWEAKR that are useful in practicing the invention also include covalent or aggregative conjugates of a TWEAKR polypeptide with other polypeptides added to provide novel polyfunctional entities.

TWEAKR Antibodies

One aspect of the present invention relates to the antigenic epitopes of the TWEAKR extracellular domain. Such epitopes are useful for raising antibodies, and in particular the blocking monoclonal antibodies described in more detail below. Such epitopes or variants thereof can be produced using techniques well known in the art such as solid-phase synthesis, chemical or enzymatic cleavage of a polypeptide, or using recombinant DNA technology.

The claimed invention encompasses compositions and uses of antibodies that are immunoreactive with TWEAKR polypeptides. Such antibodies "bind specifically" to TWEAKR polypeptides, meaning that they bind via antigen-binding sites of the antibody as compared to non-specific binding interactions. The terms "antibody" and "antibodies" are used herein in their broadest sense, and include, without limitation, intact monoclonal and polyclonal antibodies as well as fragments such as Fv, Fab, and F(ab')2 fragments, single-chain antibodies such as scFv, and various chain combinations. The antibodies of the present invention are preferably humanized, and more preferably human. The antibodies may be prepared using a variety of well-known methods including, without limitation, immunization of animals having native or transgenic immune repertoires, phage display, hybridoma and recombinant cell culture, and transgenic plant and animal bioreactors.

Both polyclonal and monoclonal antibodies may be prepared by conventional techniques. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988).

Hybridoma cell lines that produce monoclonal antibodies specific for the polypeptides of the invention are also contemplated herein. Such hybridomas may be produced and identified by conventional techniques. One method for producing such a hybridoma cell line comprises immunizing an animal with a polypeptide, harvesting spleen cells from the immunized animal, fusing said spleen cells to a myeloma cell line, thereby generating hybridoma cells, and identifying a hybridoma cell line that produces a monoclonal antibody that binds the polypeptide. The monoclonal antibodies produced by hybridomas may be recovered by conventional techniques.

The monoclonal antibodies of the present invention include chimeric antibodies, e.g., "humanized" versions of antibodies originally produced in mice or other non-human species. A humanized antibody is an engineered antibody that typically comprises the variable region of a non-human (e.g., murine) antibody, or at least complementarity determining regions (CDRs) thereof, and the remaining immunoglobulin portions derived from a human antibody. Procedures for the production of chimeric and further engineered monoclonal antibodies include those described in Riechmann et al. (*Nature* 332:323, 1988), Liu et al. (PNAS 84:3439, 1987), Larrick et al. (*Bio/Technology* 7:934, 1989), and Winter and Harris (TIPS 14:139, May, 1993). Such humanized antibodies may be prepared by known techniques and offer the advantage of reduced immunogenicity when the antibodies are administered to humans.

Procedures that have been developed for generating human antibodies in non-human animals may be employed in producing antibodies of the present invention. The antibodies may be partially human or preferably completely human. For example, transgenic mice into which genetic material encoding one or more human immunoglobulin chains has been introduced may be employed. Such mice may be genetically altered in a variety of ways. The genetic manipulation may result in human immunoglobulin polypeptide chains replacing endogenous immunoglobulin chains in at least some, and preferably virtually all, antibodies produced by the animal upon immunization.

Mice in which one or more endogenous immunoglobulin genes have been inactivated by various means have been prepared and are commercially available from, for example, Medarex Inc. (Princeton, N.J.) and Abgenix Inc. (Fremont, Calif.). Human immunoglobulin genes have been introduced into the mice to replace the inactivated mouse genes. Antibodies produced in the animals incorporate human immunoglobulin polypeptide chains encoded by the human genetic material introduced into the animal. Examples of techniques for the production and use of such transgenic animals to make antibodies (which are sometimes called "transgenic antibodies") are described in U.S. Pat. Nos. 5,814,318, 5,569,825, and 5,545,806, which are incorporated by reference herein.

Inhibitory Antisense, Ribozyme, and Triple Helix Approaches

Modulation of angiogenesis in a tissue or group of cells may also be ameliorated by decreasing the level of TWEAKR gene expression and/or TWEAKR-ligand interaction by using TWEAKR or ligand gene sequences in conjunction with well-known antisense, gene "knock-out," ribozyme and/or triple helix methods to decrease the level of TWEAKR or ligand gene expression. Among the compounds that may exhibit the ability to modulate the activity, expression or synthesis of the TWEAKR or a ligand gene, including the ability to modulate angiogenesis, are antisense, ribozyme, and triple helix molecules. Such molecules may be designed to reduce or inhibit either unimpaired, or if appropriate, mutant target gene activity. Techniques for the production and use of such molecules are known to those of skill in the art.

Recombinant Production of TWEAKR Polypeptides

TWEAKR polypeptides, including soluble TWEAKR polypeptides, fragments, and fusion polypeptides, used in the present invention may be prepared using a recombinant expression system. Host cells transformed with a recombinant expression vector or a polynucleotide encoding a TWEAKR polypeptide, soluble TWEAKR polypeptide, or fusion polypeptide ("recombinant host cells") are cultured under conditions that promote expression of TWEAKR molecule and the TWEAKR molecule is recovered. TWEAKR polypeptides can also be produced in transgenic plants or animals, or by chemical synthesis.

TWEAKR Nucleic Acids

The invention encompasses nucleic acid molecules (i.e., polynucleotides) encoding a TWEAKR polypeptide used in the invention, including: (a) nucleic acids that encode residues from about 28 to $x_1$, ($x_1$ is residue 68, 69, 70, 71, 72, 73, 74, 75, 76, 77, 78, 79 or 80) of SEQ ID NO:4 and fragments thereof that bind TWEAK; (b) nucleic acids that are at least 70%, 80%, 90%, 95%, 98%, or 99% identical to a nucleic acid of (a), and which encode a polypeptide capable of binding TWEAK; and (c) nucleic acids that hybridize at moderate stringency to a nucleic acid of (a), and which encode a polypeptide capable of binding TWEAK.

Due to degeneracy of the genetic code, there can be considerable variation in nucleotide sequences encoding the same amino acid sequence. Included as embodiments of the invention are nucleic acid sequences capable of hybridizing under moderately stringent conditions (e.g., prewashing solution of 5× SSC, 0.5% SDS, 1.0 mM EDTA (pH 8.0) and hybridization conditions of 50° C., 5× SSC, overnight) to the DNA sequences encoding TWEAKR. The skilled artisan can determine additional combinations of salt and temperature that constitute moderate hybridization stringency (see also, Sambrook, *Molecular Cloning: A Laboratory Manual*, Cold Spring Harbor Laboratory Press, 1989; Maniatis, *Molecular Cloning: A Laboratory Manual*, Cold Spring Harbor Laboratory Press, 1982; and Ausubel, *Current Protocols in Molecular Biology*, Wiley and Sons, 1989 and later versions, which are incorporated herein by reference). Conditions of higher stringency include higher temperatures for hybridization and post-hybridization washes, and/or lower salt concentration. Percent identity of nucleic acids may be determined using the methods described above for polypeptides, e.g., by methods including visual inspection and/or the use of computer programs such as GAP.

Any suitable expression system may be employed for the production of recombinant TWEAKR. Recombinant expression vectors include nucleic acids (e.g., DNA or RNA) encoding a TWEAKR polypeptide operably linked to suitable transcriptional and translational regulatory nucleotide sequences, such as those derived from a mammalian, microbial, viral, or insect gene. A TWEAKR nucleic acid molecule and a regulatory sequence are operably linked when the regulatory sequence functionally relates to the TWEAKR nucleic acid molecule. Thus, a regulatory sequence such as a promoter is operably linked to a TWEAKR nucleic acid molecule if the promoter controls the transcription of the TWEAKR nucleic acid molecule. Examples of regulatory sequences include transcriptional promoters, operators, or enhancers, an mRNA ribosomal binding site, internal ribosome entry sites (IRES), and appropriate sequences which control transcription and translation initiation and termination. A sequence encoding an appropriate signal peptide (native or heterologous) can be incorporated into expression vectors. A DNA sequence for a signal peptide (referred to by a variety of names including secretory leader, leader peptide, or leader) may be fused in frame to the TWEAKR sequence so that the TWEAKR polypeptide is initially translated as a fusion protein comprising the signal peptide. A signal peptide that is functional in the intended host cells promotes extracellular secretion of the TWEAKR polypeptide. The signal peptide is cleaved from the TWEAKR polypeptide upon secretion of TWEAKR from the cell.

Suitable host cells for expression of TWEAKR polypeptides include prokaryotes, yeast, and higher eukaryotic cells, including insect and mammalian cells. Appropriate cloning and expression vectors for use with bacterial, fungal, yeast, insect, and mammalian cellular hosts are described, for example, in Pouwels et al. *Cloning Vectors: A Laboratory Manual*, Elsevier, New York, 1985.

Prokaryotes include gram negative or gram positive organisms, for example, *E. coli* or *Bacilli*. Suitable prokaryotic host cells for transformation include, for example, *E. coli, Bacillus subtilis, Salmonella typhiniurium*, and various other species within the genera *Pseudomonas, Streptomyces*, and *Staphylococcus*. In a prokaryotic host cell, such as *E. coli*, TWEAKR polypeptides may include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker gene(s). A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a TWEAKR DNA sequence are inserted into the pBR322 vector. Other commercially available vectors include, for example, pKK223-3 (Pharmacia Fine Chemicals, Uppsala, Sweden) and pGEMI (Promega Biotec, Madison, Wis., USA).

Promoter sequences commonly used for recombinant prokaryotic host cell expression vectors include β-lactamase (penicillinase), lactose promoter system (Chang et al., Nature 275:615, 1978; Goeddel el al., Nature 281:544, 1979), tryptophan (trp) promoter system (Goeddel et al., Nucl. Acids Res. 8:4057, 1980; EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage λ $P_L$ promoter and a cI857ts thermolabile repressor sequence. Plasmid vectors available from the American Type Culture Collection which incorporate derivatives of the λ $P_L$ promoter include plasmid pHUB2 (resident in *E. coli*, strain JMB9, ATCC 37092) and pPLc28 (resident in *E. coli*, RRI, ATCC 53082).

The stability of TWEAKR lends itself to expression in prokaryotic systems. For example, TweakR ligand binding domain will spontaneously re-fold into an active conformation even after being reduced and boiled in SDS loading buffer.

TWEAKR polypeptides may also be expressed in yeast host celfs, preferably from the *Saccharomyces* genus (e.g., *S. cerevisiae*). Other genera of yeast, such as *Pichia* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., J. Biol. Chem. 255:2073, 1980) or other glycolytic enzymes (Hess et al., J. Adv. Enzyme Reg. 7:149, 1968; Holland et al., Biochem. 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in Hitzeman, EPA-73,657. Another alternative is the glucose-repressible ADH2 promoter described by Russell et al. (J. Biol. Chem. 258:2674, 1982) and Beier et al. (Nature 300:724, 1982). Shuttle vectors replicable in both yeast and *E. coli*, may be constructed by inserting DNA sequences from pBR322 for selection and replication in *E. coli* (Amp$^r$ gene and origin of replication) into the above-described yeast vectors.

The yeast α-factor leader sequence may be employed to direct secretion of recombinant polypeptides. The α-factor leader sequence is often inserted between the promoter sequence and the structural gene sequence. See, e.g., Kurjan et al., Cell 30:933, 1982; Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Insect host cell culture systems also may be employed to express recombinant TWEAKR polypeptides, including soluble TWEAKR polypeptides. Bacculovirus systems for production of heterologous polypeptides in insect cells are reviewed by Luckow and Summers, Bio/Technology 6:47, 1988.

Mammalian cells are typically used as host cells. Examples of suitable mammalian host cell lines include the COS-7 line of monkey kidney cells (ATCC CRL 1651) (Gluzman et al., Cell 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (EMBO J. 10: 2821, 1991). For the production of therapeutic polypeptides it is particularly advantageous to use a mammalian host cell line which has been adapted to grow in media that does not contain animal proteins.

Established methods for introducing DNA into mammalian cells have been described (Kaufman, R.J., *Large Scale Mammalian Cell Culture*, 1990, pp. 15-69). Additional protocols using commercially available reagents, such as Lipofectamine (Gibco/BRL) or Lipofectamine-Plus, can be used to transfect cells (Feigner et al., Proc. Natl. Acad. Sci. USA 84:7413, 1987). In addition, electroporation can be used to transfect mammalian cells using conventional procedures, such as those in Sambrook et al. *Molecular Cloizing: A Laboratory Manual*, 2 ed. Vol. 1-3, Cold Spring Harbor Laboratory Press, 1989). Selection of stable transformants can be performed using methods known in the art, such as, for example, resistance to cytotoxic drugs. Kaufman et al., Meth. in Enzymology 185:487, 1990, describes several selection schemes, such as dihydrofolate reductase (DHFR) resistance. A suitable host strain for DHFR selection can be CHO strain DX-B11, which is deficient in DHFR (Urlaub and Chasin, Proc. Natl. Acad. Sci. USA 77:4216, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., Nature 273:113, 1978; Kaufman, Meth. in Enzymology, 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology*, 1997, pp. 529-534) and the tripartite leader (TPL) and VA gene RNAs from Adenovirus 2 (Gingeras et al., J. Biol. Chem. 257:13475, 1982). The internal ribosome entry site (IRES) sequences of viral origin allows dicistronic mRNAs to be translated efficiently (Oh and Sarnow, Current Opinion in Genetics and Development 3:295, 1993; Ramesh et al., Nucleic Acids Research 24:2697, 1996). Expression of a heterologous cDNA as part of a dicistronic mRNA followed by the gene for a selectable marker (e.g. DHFR) has been shown to improve transfectability of the host and expression of the heterologous cDNA (Kaufman, Meth. in Enzymology, 1990). Exemplary expression vectors that employ dicistronic mRNAs are pTR-DC/GFP described by Mosser et al., Biotechniques 22:150, 1997, and p2A5I described by Morris et al., *Animal Cell Technology*, 1997, pp. 529-534.

A useful high expression vector, pCAVNOT, has been described by Mosley et al., Cell 59:335, 1989. Other expression vectors for use in mammalian host cells can be constructed as disclosed by Okayama and Berg (Mol. Cell. Biol. 3:280, 1983). A useful system for stable high level expression of mammalian cDNAs in C127 murine mammary epithelial cells can be constructed substantially as described by Cosman et al. (Mol. Immunol. 23:935, 1986). A useful high expression vector, PMLSV N1/N4, described by Cosman et al., Nature 312:768, 1984, has been deposited as ATCC 39890. Additional useful mammalian expression vectors are known in the art.

Regarding signal peptides that may be employed in producing TWEAKR polypeptides, the native TWEAKR signal peptide may used or it may be replaced by a heterologous signal peptide or leader sequence, if desired. The choice of signal peptide or leader may depend on factors such as the type of host cells in which the recombinant TWEAKR is to be produced. Examples of heterologous signal peptides that are functional in mammalian host cells include the signal sequence for interleukin-7 (IL-7) described in U.S. Pat. No. 4,965,195, the signal sequence for interleukin-2 receptor described in Cosman et al., Nature 312:768 (1984); the interleukin-4 receptor signal peptide described in EP 367,566; the type I interleukin-1 receptor signal peptide described in U.S.

Pat. No. 4,968,607; and the type 11 interleukin-1 receptor signal peptide described in EP 460,846.

Using the techniques of recombinant DNA including mutagenesis, directed evolution, and the polymerase chain reaction (PCR) (see, e.g., U.S. Pat. Nos. 6,171,820 and 6,238,884), the skilled artisan can produce DNA sequences that encode TWEAKR polypeptides comprising various additions or substitutions of amino acid residues or sequences, or deletions of terminal or internal residues or sequences, including TWEAKR fragments, variants, derivatives, and fusion polypeptides.

Transgenic animals, including mice, goats, sheep, and pigs, and transgenic plants, including tobacco, tomato, legumes, grasses, and grains, may also be used as bioreactors for the production of TWEAKR polypeptides, including soluble TWEAKR polypeptides. In the case of transgenic animals, it is particularly advantageous to construct a chimeric DNA including a TWEAKR coding sequence operably linked to cis-acting regulatory sequences that promote expression of the soluble TWEAKR in milk and/or other body fluids (see, e.g., U.S. Pat. Nos. 5,843,705; 5,880,327). In the case of transgenic plants it is particularly advantageous to produce TWEAKR in a particular cell type, tissue, or organ (see, e.g., U.S. Pat. Nos. 5,639,947; 5,889,189).

The skilled artisan will recognize that the procedure for purifying expressed soluble TWEAKR polypeptides will vary according to the host system employed, and whether or not the recombinant polypeptide is secreted. Soluble TWEAKR polypeptides may be purified using methods known in the art, including one or more concentration, salting-out, ion exchange, hydrophobic interaction, affinity purification, HPLC, or size exclusion chromatography steps. Fusion polypeptides comprising Fc moieties (and multimers formed therefrom) offer the advantage of facile purification by affinity chromatography over Protein A or Protein G columns.

Methods of Treatment

Described below are methods and compositions employing the TWEAK receptor or ligand, or the genes encoding the TWEAK receptor or ligand, to promote or suppress angiogenesis in a subject, a target tissue, or a group of cells. The terms "treat," "treating," "treatment," "therapy," "therapeutic," and the like are intended to include preventative therapy, prophylactic therapy, ameliorative therapy, and curative therapy. By "subject" is meant any mammal (e.g., bovine, equine, porcine, canine, feline, and primates), but preferably is a human.

The disclosed polypeptides, compositions, and methods are used to inhibit angiogenesis, modulate cell migration and/or proliferation, or other TWEAKR-mediated responses in a subject in need of such treatment. The term "TWEAKR-mediated response" includes any cellular, physiological, or other biological response that is caused at least in part by the binding of TWEAK ligand to TWEAKR, or which may be inhibited or suppressed, in whole or in part, by blocking TWEAK from binding to TWEAKR. The treatment is advantageously administered in order to prevent the onset or the recurrence of a disease or condition mediated by angiogenesis, or to treat a subject that has a disease or condition mediated by angiogenesis. Diseases and conditions mediated by angiogenesis include but are not limited to ocular disorders, malignant and metastatic conditions, and inflammatory diseases. In some instances stimulation of a TWEAK-TWEAKR response may be beneficial (e.g., during tissue or would repair). Accordingly, administration of TWEAK or TWEAKR in such tissue or cells may be used to promote wound repair.

Among the ocular disorders that can be treated according to the present invention are eye diseases characterized by ocular neovascularization including, but not limited to, diabetic retinopathy (a major complication of diabetes), retinopathy of prematurity (this devastating eye condition, that frequently leads to chronic vision problems and carries a high risk of blindness, is a severe complication during the care of premature infants), neovascular glaucoma, retinoblastoma, retrolental fibroplasia, rubeosis, uveitis, macular degeneration, and corneal graft neovascularization. Other eye inflammatory diseases, ocular tumors, and diseases associated with choroidal or iris neovascularization can also be treated according to the present invention.

The present invention can also be used to treat cell proliferative disorders, including malignant and metastatic conditions such as solid tumors. Solid tumors include both primary and metastatic sarcomas and carcinomas.

The present invention can also be used to treat inflammatory diseases including, but not limited to, arthritis, rheumatism, and psoriasis.

Other diseases and conditions that can be treated according to the present invention include benign tumors and preneoplastic conditions, myocardial angiogenesis, hemophilic joints, scleroderma, vascular adhesions, atherosclerotic plaque neovascularization, telangiectasia, and wound granulation.

Disease states that are angiogenic-dependent include coronary or peripheral atherosclerosis and ischemia of any tissue or organ, including the heart, liver, brain, and the like. These types of diseases can be treated by compositions that promote angiogenesis.

In addition to polypeptides comprising a fragment of TWEAKR extracellular domain, soluble TWEAKR multimers, and antibodies that bind to the TWEAKR extracellular domain, other forms of TWEAKR antagonists can also be administered to achieve a therapeutic effect. Examples of other forms of TWEAKR antagonists include other antibodies such as antibodies against TWEAK, antisense nucleic acids, ribozymes, muteins, aptamers, and small molecules directed against TWEAKR or against TWEAK.

The methods according to the present invention can be tested in vivo animal models to confirm the desired prophylactic or therapeutic activity, as well as to determine the optimal therapeutic dosage, prior to administration to humans.

The amount of a particular TWEAKR antagonist that will be effective in a particular method of treatment depends upon age, type and severity of the condition to be treated, body weight, desired duration of treatment, method of administration, and other parameters. Effective dosages are determined by a physician or other qualified medical professional. Typical effective dosages are about 0.01 mg/kg to about 100 mg/kg body weight. In some preferred embodiments the dosage is about 0.1-50 mg/kg; in some preferred embodiments the dosage is about 0.5-10 mg/kg. The dosage for local administration is typically lower than for systemic administration. In some embodiments a single administration is sufficient; in some embodiments the TWEAKR antagonist is administered as multiple doses over one or more days.

The TWEAKR antagonists are typically administered in the form of a pharmaceutical composition comprising one or more pharmacologically acceptable carriers. Pharmaceutically acceptable carriers include diluents, fillers, adjuvants, excipients, and vehicles that are pharmaceutically acceptable for the route of administration, and may be aqueous or oleaginous suspensions formulated using suitable dispersing, wetting, and suspending agents.

Pharmaceutically acceptable carriers are generally sterile and free of pyrogenic agents, and may include water, oils, solvents, salts, sugars and other carbohydrates, emulsifying agents, buffering agents, antimicrobial agents, and chelating agents. The particular pharmaceutically acceptable carrier and the ratio of active compound to carrier are determined by the solubility and chemical properties of the composition, the mode of administration, and standard pharmaceutical practice.

The compositions as described herein may be contained in a vial, bottle, tube, syringe inhaler or other container for single or multiple administrations. Such containers may be made of glass or a polymer material such as polypropylene, polyethylene, or polyvinylchloride, for example. Preferred containers may include a seal or other closure system, such as a rubber stopper that may be penetrated by a needle in order to withdraw a single dose and then re-seal upon removal of the needle. All such containers for injectable liquids, lyophilized formulations, reconstituted lyophilized formulations or reconstitutable powders for injection known in the art or for the administration of aerosolized compositions are contemplated for use in the presently disclosed compositions and methods.

The TWEAKR antagonists are administered to the subject in a manner appropriate to the indication. Thus, for example, a TWEAKR antagonist, or a pharmaceutical composition thereof, may be administered by intravenous, transdermal, intradermal, intraperitoneal, intramuscular, intranasal, epidural, oral, topical, subcutaneous, intracavity, sustained release from implants, peristaltic routes, or by any other suitable technique. Parenteral administration is preferred.

In certain embodiments of the claimed invention, the treatment further comprises treating a subject with one or more additional agents such as additional chemotherapeutic agents. The additional chemotherapeutic agent(s) may be administered prior to, concurrently with, or following the administration of the TWEAKR antagonist. The use of more than one chemotherapeutic agent is particularly advantageous when the subject that is being treated has a solid tumor. In some embodiments of the claimed invention, the treatment further comprises treating the subject with radiation. Radiation, including brachytherapy and teletherapy; may be administered prior to, concurrently with, or following the administration of the second chemotherapeutic agent(s) and/or TWEAKR antagonist.

When the subject that is being treated has a solid tumor, the method preferably includes the administration of, in addition to a TWEAKR antagonist, one or more chemotherapeutic agents selected from the group consisting of alkylating agents, antimetabolites, vinca alkaloids and other plant-derived chemotherapeutics, nitrosoureas, antitumor antibiotics, antitumor enzymes, topoisomerase inhibitors, platinum analogs, adrenocortical suppressants, hormones, hormone agonists and antagonists, antibodies, immunotherapeutics, blood cell factors, radiotherapeutics, and biological response modifiers.

In some preferred embodiments the method includes administration of, in addition to a TWEAKR antagonist, one or more chemotherapeutic agents selected from the group consisting of cisplatin, cyclophosphamide, mechloretamine, melphalan, bleomycin, carboplatin, fluorouracil, 5-fluorodeoxyuridine, methotrexate, taxol, asparaginase, vincristine, and vinblastine, lymphokines and cytokines such as interleukins, interferons (including alpha, beta, or delta), and TNF, chlorambucil, busulfan, carmustine, lomustine, semustine, streptozocin, dacarbazine, cytarabine, mercaptopurine, thioguanine, vindesine, etoposide, teniposide, dactinomycin, daunorubicin, doxorubicin, bleomycin, plicamycin, mitomycin, L-asparaginase, hydroxyurea, methylhydrazine, mitotane, tamoxifen, and fluoxymesterone.

In some preferred embodiments the method includes administration of, in addition to a TWEAKR antagonist, one or more chemotherapeutic agents, including various soluble forms thereof, selected from the group consisting of Flt3 ligand, CD40 ligand, interleukin-2, interleukin-12, 4-1BB ligand, anti-4-1BB antibodies, TNF antagonists and TNF receptor antagonists, TRAIL, VEGF antagonists, VEGF receptor (including VEGF-R1 and VEGF-R2, also known as Flt1 and Flk1 or KDR) antagonists, Tek antagonists, and CD148 (also referred to as DEP-1, ECRTP, and PTPRJ, see Takahashi et al., J. Am. Soc. Nephrol. 10:2135-45, 1999) agonists. In some preferred embodiments the TWEAKR antagonists of the invention are used as a component of, or in combination with, "metronomic therapy," such as that described by Browder et al. and Klement et al. (Cancer Research 60:1878, 2000; J. Clin. Invest. 105(8):R15, 2000; see also Barinaga, Science 288:245, 2000).

The polypeptides, compositions, and methods of the present invention may be used as a first line treatment, for the treatment of residual disease following primary therapy, or as an adjunct to other therapies including chemotherapy, surgery, radiation, and other therapeutic methods known in the art.

When the nucleic acid sequences of the present invention are delivered according to the methods disclosed herein, it is advantageous to use a delivery mechanism so that the sequences will be incorporated into a cell for expression. Delivery systems that may advantageously be employed in the contemplated methods include the use of, for example, viral delivery systems such as retroviral and adenoviral vectors, as well as non-viral delivery systems. Such delivery systems are well known by those skilled in the art.

Methods of Screening

TWEAKR as described herein may be used in a variety of methods of screening to isolate, for example, TWEAKR agonists and antagonists. TWEAKR agonists are compounds that promote the biological activity of TWEAKR and TWEAKR antagonists are compounds that inhibit the biological activity of TWEAKR. Compounds identified via the following screening assays can be used in compositions and methods for modulating angiogenesis to treat a variety of disease states. The present invention provides methods of screening for compounds that (1) modulate TWEAKR or ligand gene expression in a target tissue or cell, (2) modulate the TWEAKR-ligand interaction to regulate angiogenesis; (3) bind to the TWEAKR or ligand to influence angiogenesis; or (4) interfere with or regulate the bound TWEAKR-ligand complex's influence on downstream events such as angiogenesis. Accordingly, the polypeptides, and fragments thereof, of the invention can be used to regulate, influence, and modulate (i.e., increase or decrease) a biological activity associated with interaction of TWEAK or TWEAKR with its cognate.

The present invention contemplates the use of assays that are designed to identify compounds that modulate the activity of a TWEAKR or ligand gene (e.g., modulate the level of TWEAKR or TWEAK gene expression and/or modulate the level of TWEAKR or TWEAK gene product activity). Assays may additionally be utilized that identify compounds that bind to TWEAKR or TWEAK gene regulatory sequences (e.g., promoter sequences; see e.g., Platt, 1994, J. Biol. Chem.

269, 28558-28562), and that may modulate the level of TWEAKR or TWEAK gene expression.

Such an assay may involve, for example, the use of a control system, in which transcription and translation of the TWEAKR or ligand gene occurs, in comparison to a system including a test agent suspected of influencing normal transcription or translation of a TWEAKR or ligand gene. For example, one could determine the rate of TWEAKR RNA produced by cardiac cells, and use this to determine if a test agent influences that rate. To assess the influence of a test agent suspected to influence this normal rate of transcription, one would first determine the rate of TWEAKR RNA production in a cardiac cell culture by, for example, Northern Blotting. One could then administer the test agent to a cardiac cell culture under otherwise identical conditions as the control culture. The rate of TWEAKR RNA in the culture treated with the test agent could be determined by, for example, Northern Blotting, and compared to the rate of TWEAKR RNA produced by the control culture cells. An increase in the TWEAKR RNA in the cells contacted with the test agent relative to control cells is indicative of a stimulator of TWEAKR gene transcription in cardiac cells, while a decrease is indicative of an inhibitor of TWEAKR gene transcription in cardiac cells.

There are a variety of other methods that can be used to determine the level of TWEAKR or ligand gene expression as well, and may further be used in assays to determine the influence of a test agent on the level of TWEAKR or ligand gene expression. For example, RNA from a cell type or tissue known, or suspected, to express the TWEAK receptor or ligand gene, such as cardiac tissue, may be isolated and tested utilizing hybridization or PCR techniques. The isolated cells can be derived from cell culture or from a subject. The analysis of cells taken from culture may be a necessary step in the assessment of cells to be used as part of a cell-based gene therapy technique or, alternatively, to test the effect of compounds on the expression of the TWEAK receptor or ligand gene. Such analyses may reveal both quantitative and qualitative aspects of the expression pattern of the TWEAK receptor or ligand gene, including activation or inactivation of TWEAKR or ligand gene expression.

In one embodiment of such a detection scheme, a cDNA molecule is synthesized from an RNA molecule of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the TWEAKR or ligand gene nucleic acid segments described above. The preferred lengths of such nucleic acid reagents are at least 9-30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Additionally, it is possible to perform such TWEAKR or ligand gene expression assays "in situ", i.e., directly upon tissue sections (fixed and/or frozen) of subject tissue obtained from biopsies or resections, such that no nucleic acid purification is necessary. TWEAKR or ligand gene nucleic acid segments described above can be used as probes and/or primers for such in situ procedures (see, for example, Nuovo, G. J., 1992, "PCR In situ Hybridization: Protocols And Applications", Raven Press, NY).

Compounds identified via assays such as those described herein may be useful, for example, in modulating angiogenesis influenced by TWEAKR or TWEAKR-ligand interaction. Such methods of stimulating or inhibiting TWEAK- or TWEAKR-influenced angiogenesis are discussed herein.

Alternatively, assay systems may be designed to identify compounds capable of binding the TWEAKR or ligand polypeptide of the invention and thereby influencing angiogenesis resulting from this interaction. Compounds identified may be useful, for example, in modulating the vascularization of target tissues or cells, may be utilized in screens for identifying compounds that disrupt normal TWEAKR-ligand interactions, or may in themselves disrupt such interactions.

The principle of the assays used to identify compounds that bind to the TWEAK receptor or ligand involves preparing a reaction mixture of the TWEAK receptor or ligand and the test agent under conditions and for a time sufficient to allow the two components to interact or bind, thus forming a complex that can be removed and/or detected in the reaction mixture. These assays can be conducted in a variety of ways. For example, one method to conduct such an assay screening for compounds that bind to the TWEAK receptor, would involve anchoring the TWEAK receptor or the test substance onto a solid phase and detecting TWEAKR/test agent complexes anchored on the solid phase at the end of the reaction. In one embodiment of such a method, the TWEAK receptor may be anchored onto a solid surface, and the test agent, which is not anchored, may be labeled, either directly or indirectly. Alternatively, these same methods could be used to screen for test agents that bind to the TWEAK ligand rather than receptor.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for the TWEAK receptor or ligand or the test agent to anchor any complexes formed in solution, and a labeled antibody specific for the other component of the possible complex to detect anchored complexes.

Those compounds identified as binding agents for either the TWEAK receptor or the TWEAK ligand may further be assessed for their ability to interfere with TWEAKR-ligand interaction, as described below, and thereby suppress or promote angiogenesis resulting from TWEAKR-ligand interaction. Such compounds may then be used therapeutically to stimulate or inhibit angiogenesis.

The TWEAKR and ligand polypeptides of the present invention may also be used in a screening assay to identify compounds and small molecules which specifically interact with the disclosed TWEAK receptor or ligand to either inhibit (antagonize) or enhance (agonize) interaction between these molecules. Thus, for example, polypeptides of the invention may be used to identify antagonists and agonists from cells, cell-free preparations, chemical libraries, and natural product mixtures. The antagonists and agonists may be natural or modified substrates, ligands, enzymes, receptors, and the like, of the polypeptides of the instant invention, or may be structural or functional mimetics of the polypeptides. Potential antagonists of the TWEAKR-ligand interaction of the instant invention may include small molecules, polypeptides, peptides, peptidomimetics, and antibodies that bind to and occupy a binding site of the polypeptides, causing them to be unavailable to interact and therefore preventing their normal ability to modulate angiogenesis. Other potential antagonists are antisense molecules that may hybridize to mRNA in vivo and block translation of the mRNA into the polypeptides of the instant invention. Potential agonists include small molecules, polypeptides, peptides, peptidomimetics, and antibodies that bind to the instant TWEAKR and TWEAK polypeptides and influence angiogenesis as caused by the disclosed interactions of the TWEAKR and TWEAK polypeptides of the instant invention.

Small molecule agonists and antagonists are usually less than 10K molecular weight and may possess a number of physiochemical and pharmacological properties that enhance cell penetration, resist degradation and prolong their physiological half-lives. (Gibbs, "Pharmaceutical Research in Molecular Oncology," Cell, Vol. 79, (1994)). Antibodies, which include intact molecules as well as fragments such as Fab and F(ab')2 fragments, may be used to bind to and inhibit the polypeptides of the instant invention by blocking the commencement of a signaling cascade. It is preferable that the antibodies are humanized, and more preferable that the antibodies are human. The antibodies of the present invention may be prepared by any of a variety of well-known methods. Alternatively, antibodies may bind to and activate the polypeptides of the instant by mimicking the interaction of a polypeptide of the invention with its cognate. One of skill in the art using the assay methods and techniques herein can determine whether an antibody is. an antagonist or agonist.

Specific screening methods are known in the art and many are extensively incorporated in high throughput test systems so that large numbers of test agents can be screened within a short amount of time. The assays can be performed in a variety of formats, including protein-protein binding assays, biochemical screening assays, immunoassays, cell based assays, and the like. These assay formats are well known in the art. The screening assays of the present invention are amenable to screening of chemical libraries and are suitable for the identification of small molecule drug candidates, antibodies, peptides and other antagonists and agonists.

One embodiment of a method for identifying molecules which antagonize or inhibit TWEAKR-ligand interaction involves adding a candidate molecule to a medium which contains cells that express the polypeptides of the instant invention; changing the conditions of said medium so that, but for the presence of the candidate molecule, the polypeptides would interact; and observing the binding and inhibition of angiogenesis. Binding of the TWEAK receptor and ligand can be determined according to competitive binding assays outlined above, and well known in the art. The angiogenic effect of this binding can be determined via cell proliferation assays such as, for example, cell density assays, corneal pocket assays, or other cell proliferation assays that are also well-known in the art. The activity of the cells contacted with the candidate molecule may then be compared with the identical cells, which were not contacted, and agonists and antagonists of the TWEAK polypeptide interactions of the instant invention may be identified. The measurement of biological activity may be performed by a number of well-known methods such as measuring the amount of protein present (e.g. an Enzyme-Linked Immunosorbent Assay (ELISA)), production of cytokines (e.g., IL-8 and IL-6; see, e.g., Saas et al., Glia 32(1):102-7, 2000), or of the protein's activity. A decrease in biological stimulation or activation would indicate an antagonist. An increase would indicate an agonist.

Screening assays can further be designed to find molecules that mimic the biological activity resulting from the TWEAKR and/or TWEAK polypeptide interactions of the instant invention. Molecules which mimic the biological activity of a polypeptide may be useful for enhancing the biological activity of the polypeptide. To identify compounds for therapeutically active agents that mimic the biological activity of a polypeptide, it must first be determined whether a candidate molecule binds to the polypeptide. A binding candidate molecule is then added to a biological assay to determine its biological effects. The biological effects of the candidate molecule are then compared to those of the polypeptide.

Additionally, complex formation within reaction mixtures containing the test agent and normal TWEAKR or ligand gene protein may also be compared to complex formation within reaction mixtures containing the test agent and a mutant TWEAKR or ligand gene protein. This comparison may be important in those cases wherein it is desirable to identify compounds that disrupt interactions of mutant but not normal TWEAKR or ligand gene proteins.

The assay for compounds that interfere with the interaction of the TWEAKR or ligand gene products and binding partners can be conducted in a heterogeneous or homogeneous format. Heterogeneous assays involve anchoring either TWEAKR or ligand gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test agents that interfere with the interaction between the TWEAKR or ligand gene products and the binding partners, e.g., by competition, can be identified by conducting the reaction in the presence of the test substance; e.g., by adding the test substance to the reaction mixture prior to or simultaneously with the TWEAKR and ligand gene products. Alternatively, test agents that disrupt preformed complexes, e.g., compounds with higher binding constants that displace one of the components from the complex, can be tested by adding the test agent to the reaction mixture after complexes have been formed.

In a particular embodiment, the TWEAKR or ligand gene product can be prepared for immobilization using recombinant DNA techniques. For example, the TWEAKR or ligand coding region can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art. This antibody can be labeled with the radioactive isotope $^{125}$I, for example, by methods routinely practiced in the art. In a heterogeneous assay, e.g., the GST-TWEAKR or ligand fusion protein can be anchored to glutathione-agarose beads. The TWEAKR or ligand gene product can then be added in the presence or absence of the test agent in a manner that allows interaction and binding to occur. At the end of the reaction period, unbound material can be washed away, and the labeled monoclonal antibody can be added to the system and allowed to bind to the complexed components. The interaction between the TWEAKR and ligand gene products can be detected by measuring the amount of radioactivity that remains associated with the glutathione-agarose beads. A successful inhibition of the interaction by the test agent will result in a decrease in measured radioactivity.

Alternatively, a GST-TWEAKR gene fusion protein and TWEAK ligand gene product (or vice versa) can be mixed together in liquid in the absence of the solid glutathione-agarose beads. The test agent can be added either during or after the species is allowed to interact. This mixture can then be added to the glutathione-agarose beads and unbound material is washed away. Again the extent of inhibition of the TWEAKR-ligand gene product interaction can be detected by adding the labeled antibody and measuring the radioactivity associated with the beads.

In another embodiment of the invention, these same techniques can be employed using peptide fragments that correspond to the binding domains of the TWEAKR and/or ligand protein, in place of one or both of the full-length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the segments can be engineered to express peptide fragments of the protein, which can then be tested for binding activity and purified or synthesized.

As an example, and not by way of limitation, a TWEAKR or ligand gene product can be anchored to a solid material, as described above, by making a GST-TWEAKR or ligand fusion protein and allowing it to bind to glutathione agarose beads. The interactive binding partner obtained can be labeled with a radioactive isotope, such as $^{35}$S, and cleaved with a proteolytic enzyme such as trypsin. Cleavage products can then be added to the anchored GST-TWEAKR fusion protein or TWEAK ligand fusion protein and allowed to bind. After washing away unbound peptides, labeled bound material, representing the binding partner binding domain, can be eluted, purified, and analyzed for amino acid sequence by well-known methods. Peptides so identified can be produced synthetically or fused to appropriate facilitative proteins using recombinant DNA technology.

The TWEAKR-ligand interactions of the invention, in vivo, initiate a cascade of events that either stimulate or suppress angiogenesis in a target group of cells or tissues. Molecules, such as nucleic acid molecules, proteins, or small molecules may, in turn, influence this cascade. Compounds that disrupt the TWEAKR-ligand interaction may be useful in regulating angiogenesis.

The basic principle of the assay systems used to identify compounds that interfere with the angiogenic or anti-angiogenic effect of TWEAKR-ligand interaction involves preparing a reaction mixture containing the TWEAK receptor and ligand under conditions and for a time sufficient to allow the two to interact or bind, thus forming a complex. In order to test a compound for inhibitory activity of the effect of this interaction, the reaction mixture is prepared in the presence and absence of the test agent. The test agent may be initially included in the reaction mixture, or may be added at a time subsequent to the addition of the TWEAKR-ligand complex. Control reaction mixtures are incubated without the test agent or with a placebo. The inhibition or potentiation of any effect of the TWEAK complex on vascularization is then detected. Normal angiogenic response in the control reaction, but not in the reaction mixture containing the test agent, indicates that the compound interferes with the cascade of events initiated by the TWEAKR-ligand interaction. Enhanced angiogenesis in the test agents-containing culture indicates a stimulator of the TWEAKR-ligand complex effect.

In another embodiment, the techniques of rational drug design can be used to develop TWEAKR binding agents (e.g., agonist or antagonists of TWEAKR). The goal of rational drug design is to produce structural analogs of biologically active polypeptides of interest or of small molecules with which they interact, e.g., substrates, binding agents, inhibitors, agonists, antagonists, and the like. The methods provided herein can be used to fashion or identify agents which are more active or stable forms of the polypeptide or which enhance or interfere with the function of a polypeptide in vivo (Hodgson J (1991) Biotechnology 9:19-21, incorporated herein by reference). In one approach, the three-dimensional structure of a TWEAKR polypeptide of the invention, a ligand or binding partner, or of a polypeptide-binding partner complex, is determined by x-ray crystallography, by nuclear magnetic resonance, or by computer homology modeling or, most typically, by a combination of these approaches. Both the shape and charges of the polypeptide are ascertained to elucidate the structure and to determine active site(s) or sites of interaction of the molecule. Relevant structural information is used to design analogous molecules, to identify efficient inhibitors, or to identify small molecules that may bind to a polypeptide of the invention. Useful examples of rational drug design may include molecules which have improved activity or stability as shown by Braxton S and Wells JA (1992 Biochemistry 31:7796-7801) or which act as inhibitors, agonists, or antagonists of native peptides as shown by Athauda SB et al. (1993 J Biochem 113:742-746), incorporated herein by reference. The use of TWEAKR or TWEAK polypeptide structural information in molecular modeling software systems provides for the design of inhibitors or binding agents useful in modulating TWEAKR-TWEAK interactions or biological activity. A particular method of the invention comprises analyzing the three dimensional structure of TWEAK or TWEAKR polypeptides for likely binding/interaction sites of substrates or ligands, synthesizing a new molecule that incorporates a predictive reactive site, and assaying the new molecule as described further herein. Examples of algorithms, software, and methods for modeling substrates or binding agents based upon the three-dimensional structure of a protein are described in PCT publication W0107579A2, entitled "METHODS AND COMPOSITIONS FOR DETERMINING ENZYMATIC ACTIVITY," the disclosure of which is incorporated herein.

EXAMPLES

The following examples are intended to illustrate particular embodiments and not to limit the scope of the invention.

Example 1

Identification of the TWEAK Receptor

Expression Cloning of TWEAKR cDNA

To clone TWEAKR cDNA, an expression vector encoding a growth hormone leader, a leucine zipper multimerization domain, and the C-terminal extracellular domain of human TWEAK (see Chicheportiche et al., J. Biol. Chem. 272(51): 32401, 1997) was constructed. This expression vector, which was named pDC409-LZ-TWEAK, comprised the DNA sequence SEQ ID NO: I and encoded the polypeptide SEQ ID NO:2. pDC409-LZ-TWEAK conditioned supernatants were produced by transient transfection into CV1-EBNA cells. These supernatants were incubated with magnetic beads coated with polyclonal goat anti-mouse antibody that had previously been incubated with a mouse monoclonal antibody against the leucine zipper. Control beads were produced by mixing the coated beads with supernatants from cells transfected with empty vector.

A monolayer of COS cells grown in a T175 flask was transfected with 15 µg of DNA pools of complexity of 100,000 from a human umbilical vein endothelial cell (HUVEC) cDNA expression library. After 2 days these cells were lifted from the flask, and incubated in 1.5 mls of binding media plus 5% non-fat dried milk for 3 hours at 4° C. on a rotator wheel. Cells were pre-cleared by adding control beads and rotated at 4 degrees ° C. for an additional 45 minutes after which bead bound cells were removed with a magnet. Pre-clearing was repeated 2-3 times, then TWEAK coated beads were added to the cells and rotated 30 minutes at 4 °C. Cells binding the TWEAK beads were separated by use of a magnet and washed 4x in phosphate buffered saline (PBS). Plasmid DNA was extracted from these cells by lysing in 0.1% SDS, and electroporating the supernatants in DHIOIB cells. Colonies were grown overnight on ampicilin selective media. Transformants were pooled and used as a source of plasmid DNA for a further round of panning. After 2 rounds of panning, positive clones were picked from the resulting pool based on their ability to bind TWEAK using a slide binding protocol. Slide binding was performed as described more fully below, with the exception that TWEAKR positive slides were detected by incubation with TWEAKR conditioned supernatants followed by incubation with $^{125}$I-labled M15 anti-leucine zipper.

The human TWEAK receptor (also called TWEAKR) cDNA was determined to have the sequence SEQ ID NO:3, which encodes a 129 residue polypeptide (SEQ ID NO:4). Examination of the sequence predicts a polypeptide having an approximately 80 amino acid extracellular domain (residues 1-80 of SEQ ID NO:4, including the signal peptide, amino acids 1-27), an approximately 20 amino acid transmembrane domain (residues 81-100 of SEQ ID NO:4), and an approximately 29 amino acid intracellular domain (residues 101-129 of SEQ ID NO:4). TWEAKR is the smallest known TNF receptor family member. It has a single cysteine-rich repeat region in the extracellular domain, as compared with the 3-4 repeats of other TNF receptor family members. The TWEAKR polypeptide was previously described as a transmembrane protein encoded by a human liver cDNA clone (WO 98/55508, see also WO 99/61471), but had not been identified as the TWEAK receptor. A murine homolog, the FGF-inducible Fn14 (Meighan-Mantha et al., J. Biol. Chem. 274(46):33166, 1999), is approximately 82% identical to the human protein, as shown by the alignment in FIG. 1.

The newly identified TWEAK receptor was tested side by side with DR3 (which had been identified as the TWEAK receptor by Marsters et al., Current Biology 8:525, 1998) for the ability to bind to TWEAK.

TWEAKR Binds to TWEAK

Slides of COS cells were transfected with expression vectors containing TWEAKR, DR3, or vector without insert (control). After two days the cells were incubated with concentrated supernatants from CV-1 cells transfected with a vector encoding the leucine zipper TWEAK extracellular domain fusion protein. One hour later the cells were washed and probed with an 125I labeled antibody against the leucine-zipper domain. The slides were washed, fixed, and autoradiography was performed using x-ray film. The TWEAKR transfected cells bound significant amounts of TWEAK. TWEAK did not bind to the cells transfected with DR3 or the control cells. This experiment confirmed that the TWEAKR polypeptide identified in part A above, rather than DR3, is the major receptor for TWEAK. After discovery of the functional TWEAK receptor, other investigators also reported that DR3 is not the major receptor for TWEAK (Kaptein et al., FEBS Lett., 485(2-3):135, 2000. The TWEAK-TWEAKR binding interaction was further characterized by Scatchard analysis.

CV-1 cells were transfected with human full length TWEAK and mixed 1:30 with Raji cells, which do not express TWEAK. The cells were incubated with serial dilutions of 125-I labeled human TWEAKR-Fc for 2 hours at 4 degrees Celsius. Free and bound probe was separated by microfuging the samples through a phalate oil mixture in plastic tubes. Supernatants and pellets were gamma-counted. Scatchard analyses of TWEAK ligand binding the TWEAK receptor showed a binding affinity constant (Ka) of approximately $4.5 \times 10^8$ $M^{-1}$.

The TWEAK Receptor is Strongly Expressed in Cardiac Tissue

To determine the expression pattern of the TWEAK receptor, Northern blot analyses were performed. Human multiple tissue northern blots were purchased from Clontech (Palo Alto, Calif.) and probed with $^{32}$P labeled random primed DNA from the TWEAKR coding region. The blots were washed and autoradiography was performed using x-ray film. Results showed that in the adult TWEAKR is strongly expressed in heart, placenta, and some skeletal muscle samples. Strong expression in heart tissue further supports the utility of TWEAKR in the diagnosis and treatment of cardiac disease. In contrast to the adult, the fetal tissues expressed TWEAKR more ubiquitously; TWEAKR transcripts were seen in the lung and liver.

Example 2

Preparation of TWEAKR Antagonists and Agonists

Because TWEAK induces angiogenesis, TWEAKR agonists (such as agonistic antibodies) may be used to promote angiogenesis and TWEAKR antagonists (such as soluble receptors and antagonistic antibodies) may be used to inhibit angiogenesis.

Recombinant Production of Soluble TWEAKR-Fc Fusion Polypeptides

To construct a nucleic acid encoding the TWEAKR extracellular domain fused to Fc, a nucleic acid encoding the N-terminal 79 amino acids from TWEAKR, including the leader (signal peptide), was joined to a nucleic acid encoding an Fc portion from human IgG1. Sequences for this construct are shown as SEQ ID NO:6 and 8 (nucleic acid) and SEQ ID NO:7 and 9 (amino acid). In SEQ ID NO:7 and 9, residues 1-27 are the predicted signal peptide (predicted to be cleaved upon secretion from the cell; the actual cleavage site was identified by N-terminal sequence analysis, see below), residues 28-79 and 28-70 of SEQ ID NO:7 and 9, respectively, are from the cysteine-rich TWEAKR extracellular domain, residues 80-81 and 71-72 of SEQ ID NO:7 and 9, respectivelly, are from a BglII cloning site, and the remainder is the Fc portion. Upon insertion into a mammalian expression vector, and expression in and secretion from a mammalian host cells, these construct produced a polypeptide designated TWEAKR-Fc (SEQ ID NO:7) and TWEAKR-FcΔ9 (SEQ ID NO:9). N-terminal sequence analysis determined that the secreted polypeptides designated TWEAKR-Fc and TWEAKR-FcΔ9 had an N-terminus corresponding to residue 28 (Glu) of SEQ ID NO:7 and 9, respectively. Anti-angiogenic activity of TWEAKR-Fc was demonstrated using assays such as those described in the following examples. An analogous Fc-fusion construct was prepared using the murine TWEAKR extracellular domain.

The extracellular domain of human TWEAKR was expressed in *E. coli* as a leucine zipper dimer fusion protein. A cDNA was constructed with the aid of PCR to place an initiator Met residue next to TWEAKR DNA encoding amino acids Glu28 to Trp79. In addition, cDNA sequences were added that encoded Flag and the leucine zipper dimer at the C-terminal end. The cDNA was then ligated into an *E. coli* expression vector. The vector was designed to express recombinant protein upon induction in *E. coli*. Several promoters or transcriptional control units can be used including the $T_7$ promoter, the $P_L$ promoter, and the Tac promoter. A number of commercially available vectors are known in the art.

*E. coli* cells containing the TWEAKR-Flag-LeuZip2 were clutured and induced for expression. After several hours, E.coli cells were collected and lysed to release intracellular proteins. The *E. coli* lysate was fractionated on SDS-PAGE and Western blotted for the Flag antigen. A specific Flag reactive band was seen at approximately 12.5 kDa, the expected size of the TWEAKR-Flag-LeuZip2. Additional blots were probed with TWEAK and bands visualized with an anti-TWEAK antibody. The same 12.5 kDa band was visualized indicating the *E.coli*-expressed TWEAKR is able to bind its ligand.

Production of Antibodies that Bind the TWEAKR Extracellular Domain BALB/c mice are immunized with TWEAKR extracellular domain and spleen cells are collected and used to prepare hybridomas using standard procedures. Hybridoma supernatants are screened, using ELISA, for the ability to bind TWEAKR. Positives are cloned two times, to insure monoclonality, then isotyped and reassayed for reactivity to TWEAKR. Antibodies and antibody derivatives are also prepared using transgenic mice that express human immunoglobulins and through the use of phage display. The resulting antibodies are tested in assays such as those described in the examples below, to characterize their ability to modulate the TWEAK-TWEAKR interaction, TWEAKR signaling, angiogenesis, and other downstream biological activities.

Agonistic antibodies are used to promote TWEAK-induced biological activities such as angiogenesis, and antagonistic antibodies are used to inhibit TWEAK-induced biological activities such as angiogenesis. For some applications, the activity of antagonistic antibodies is augmented by conjugation to a radioisotope, to a plant-, fungus-, or bacterial-derived cytotoxin such as ricin A or diptheria toxin, or to another chemical poison. And because of the restricted tissue distribution of TWEAKR, antibodies that bind to TWEAKR are particularly useful as targeting agents for imaging or delivering therapeutics to the vasculature. Antibodies that bind TWEAKR can be used, for example, to target a detectable label or chemotherapeutic to the mural cells (pericytes and vascular smooth muscle cells). Detectable labels may include radioisotopes, chemiluminescent and fluorescent compounds, and enzymes. These techniques are useful, for example, in the diagnosis, staging, and treatment of neoplasms.

Example 3

Activity of TWEAKR-Fc In a Wound Closure Assay

A planar endothelial cell migration (wound closure) assay was used to quantitate the inhibition of angiogenesis by TWEAKR-Fc in vitro. In this assay, endothelial cell migration is measured as the rate of closure of a circular wound in a cultured cell monolayer. The rate of wound closure is linear, and is dynamically regulated by agents that stimulate and inhibit angiogenesis in vivo.

Primary human renal microvascular endothelial cells (HRMEC) were isolated, cultured, and used at the third passage after thawing, as described in Martin et al., In vitro Cell Dev Biol 33:261, 1997. Replicate circular lesions, "wounds," (600-800 micron diameter) were generated in confluent HRMEC monolayers using a silicon-tipped drill press. At the time of wounding the medium (Dulbecco's Modified eagle Medium (DMEM) +1% bovine serum albumin (BSA)) was supplemented with 20 ng/ml PMA (phorbol-12-myristate-13-acetate), EGF (4 ng/ml), and 0.150 to 5 µg/ml TWEAKR-Fc, or a combination of 40 ng/ml EGF and 0.150 to 5 µg/ml TWEAKR-Fc. As a control for TWEAKR-Fc indicated samples received 5 µg/ml IgG-Fc. The residual wound area was measured as a function of time (0-12 hours) using a microscope and image analysis software (Bioquant, Nashville, TN). The relative migration rate was calculated for each agent and combination of agents by linear regression of residual wound area plotted over time. The results are shown in FIGS. 2-3.

Figure 3:
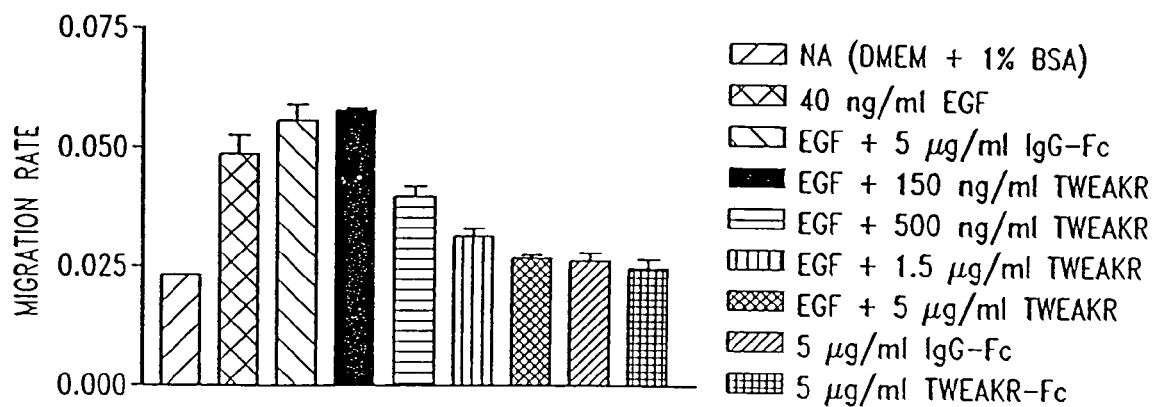
FIG. 3 shows the effect of TWEAKR-Fc on EGF-induced HRMEC wound closure.

Compared to huIgG or media+BSA, TWEAKR-Fc inhibited PMA-induced endothelial migration in a dose responsive manner, reducing the rate of migration to unstimulated levels at 1.5 to 5 µg/ml (FIG. 2). Neither huIgG nor TWEAKR-Fc inhibited basal (uninduced) migration. When HRMEC migration was induced by EGF, TWEAKR-Fc inhibited endothelial migration in a dose-dependent manner, reducing the rate of migration to unstimulated levels at 5 µg/ml (FIG. 3).

Example 4

Activity of TWEAKR-Fc In a Corneal Pocket Assay

A mouse corneal pocket assay was used to quantitate the inhibition of angiogenesis by TWEAKR-Fc in vivo. In this assay, agents to be tested for angiogenic or anti-angiogenic activity are immobilized in a slow release form in a hydron pellet, which is implanted into micropockets created in the corneal epithelium of anesthetized mice. Vascularization is measured as the appearance, density, and extent of vessel ingrowth from the vascularized corneal limbus into the normally avascular cornea.

Hydron pellets, as described in Kenyon et al., Invest Opthamol. & Visual Science 37:1625, 1996, incorporated sucralfate with basic fibroblast growth factor (bFGF) (90 ng/pellet), bFGF and IgG (14 µg/pellet, control), or bFGF and TWEAKR-Fc (14 µg). The pellets were surgically implanted into corneal stromal micropockets created by micro-dissection 1mm medial to the lateral corneal limbus of 6-8 week old male C57BL mice. After five days, at the peak of neovascular response to bFGF; the corneas were photographed, using a Zeiss slit lamp, at an incipient angle of 35-50° from the polar axis in the meridian containing the pellet. Images were digitized and processed by subtractive color filters (Adobe Photoshop 4.0) to delineate established microvessels by hemoglobin content. Image analysis software (Bioquant, Nashville, Tenn.) was used to calculate the fraction of the corneal image that was vascularized, the vessel density within the vascularized area, and the vessel density within the total cornea.

As shown in Table 1, TWEAKR-Fc (100 pmol) inhibited bFGF (3 pmol)-induced corneal angiogenesis, reducing the vascular density to 50% of that induced by FGF alone or FGF+IgG. In addition to reducing vascular area, local administration of TWEAKR-Fc significantly inhibited FGF induced vessel density (imaged on hemoglobin) by 70% compared to the vessel density in the presence of the control protein IgG-Fc.

TABLE 1

Effect of TWEAKR-Fc on FGF-induced Angiogenesis in the Mouse Corneal Pocket Assay

| Treatment | Greater than 50% Reduction in Number and Length of Vessels n/total n (%) |
| --- | --- |
| FGF alone | 0/2 (0%) |
| FGF + IgG | 0/2 (0%) |
| FGF + TWEAKR-Fc | 6/9 (67%) |

Example 5

Qualitative TRAF Binding to the TWEAK Receptor (TWEAKR) Cytoplasmic Domain

Members of the TRAF family are intra-cellular signaling molecules. Several members of the TRAF family are known to associate with members of the TNF receptor family in order to initiate a signaling cascade that activates the NF-kappa-B pathway, resulting in cell activation and proliferation. A qualitative in vitro binding assay was performed to test whether members of the TRAF family of intra-cellular signaling molecules bind to the cytoplasmic domain of TWEAKR and to learn, therefore, whether the small cytoplasmic domain of TWEAKR is capable of mediating a signal into the cell via the TRAF pathway.

A GST fusion vector consisting of the C-terminal 29 amino acids of TWEAKR fused to glutathione S-transferase was created by sub-cloning the appropriate insert into the pGEX-4T (Amersham Pharmacia Biotech) vector at the BamHI and NotI sites. The product from this vector was expressed in *E. coli* and bound to sepharose beads as described by Galibert et al., J. Biol. Chem. 273(51):34120, 1998. Similarly constructed beads coated with RANK cytoplasmic domain-GST fusion proteins were used as a positive control, and beads coated with GST alone were used as a negative control. $^{35}$S-methionine/cysteine labeled TRAF proteins were produced in reticulocyte lysates (TNT-coupled Reticulocyte Lysate Systems, Promega) according to the manufacturer's protocol. Reticulocyte lysates containing the labeled TRAF molecules were first pre-cleared using the control beads followed incubation with the indicated fusion protein coated beads in binding buffer (50 mM HEPES [pH 7.4], 250 mM NaCl, 0.25% (v/v) Nonidet P-40, 10% glycerol, 2 mM EDTA) at 4 degrees Celsius for 2 hours. After washing 4x with binding buffer bound TRAF molecules eluted from the beads in SDS-loading buffer, separated by SDS-PAGE, dried and exposed to X-ray film.

Binding above background levels was seen with TRAFS 1,2 and 3. No binding above background levels was seen with TRAFS 4,5, and 6. The ability of TWEAKR to bind to TRAFs 1,2, and 3 demonstrates that TWEAKR is capable of inducing a signal to the cell via the TRAF pathway, and therefore transmitting a proliferative signal into the host cell. This experiment provides further evidence that TWEAKR is the functional receptor for TWEAK. It also illustrates a further means by which signaling can be inhibited: by disrupting the TRAF-TWEAKR interaction with a small molecule, or by use of a dominant negative variant of the TRAF molecule.

Example 6

Activity of TWEAKR-Fc in an Endothelial Cell Proliferation Assay

An endothelial cell proliferation assay was used to quantitate the inhibition of bFGF or TWEAK induced-proliferation by TWEAKR-Fc in vitro. In this assay, endothelial cell proliferation is measured after 4 days of cell growth in microtiter wells using a cell-labeling molecule called calcein AM. Esterases expressed by the cells cleave the calcein and cause it to fluoresce when excited at 485 nm. Uncleaved calcein does not fluoresce. The amount of fluorescence is directly related to the number of endothelial cells in the culture well. Endothelial cell proliferation is often regulated by agents that stimulate and/or inhibit angiogenesis in vivo.

Primary HUVEC (human umbilical vein endothelial cells) were obtained from a commercial source (Clonetics, Walkersville, Md.), cultured, and used at passage 2 to 7. Replicate cultures were set up by adding 3000 HUVEC to each microtiter well in endothelial cell basal media (EBM, an endothelial cell basal media that contains no growth factors or serum and is based on the media formulations developed by Dr. Richard Ham at the University of Colorado, Clonetics) plus 0.05% FBS (fetal bovine serum). At the time of culture initiation FGF-2 (fibroblast growth factor-2, 10 ng/ml) or human TWEAK (100 ng/ml) was added to the cultures in the presence of human IgG (huIgG, control) or human TWEAKR-Fc at concentrations ranging from 0.08 µg/ml to 20 µg/ml (0.25 to 20 µg/ml for TWEAK-induced and 0.08 to 6.7 µg/ml for FGF-2-induced). The HUVEC containing cultures were incubated for 4 days at 37° C., 5% $CO_2$. On the fourth day of culture 4 µM calcein-AM was added to the cultures and 2 hours later the wells were evaluated for fluorescence. The results, expressed as the average fluorescence (485-530 nm) counts for replicate wells plus or minus the SEM, are shown in FIGS. 4 and 5.

Figure 4:
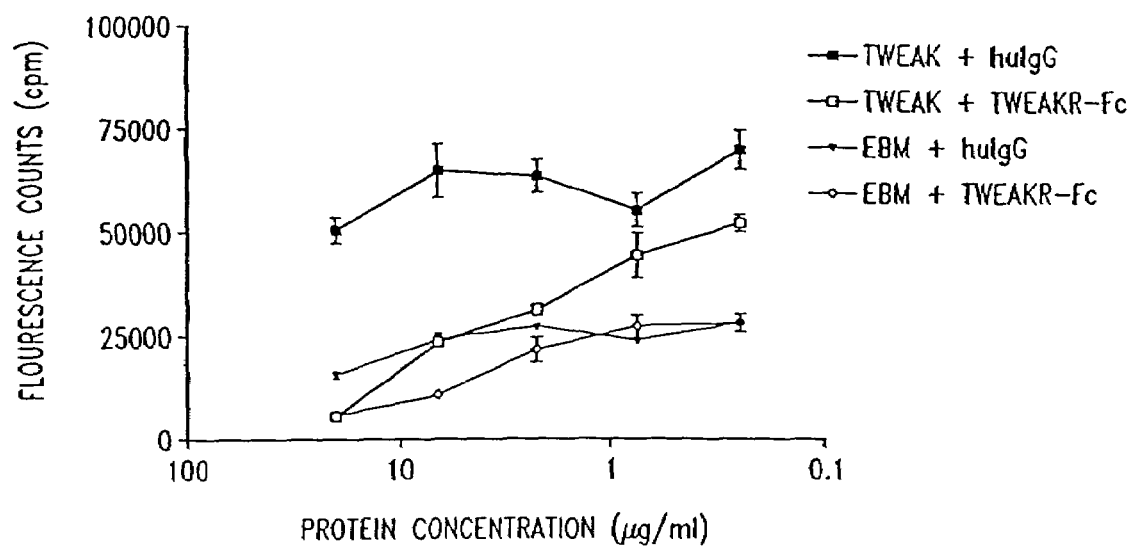
FIG. 4 shows the effect of human TWEAKR-Fc on TWEAK-induced (100 ng/ml) HUVEC proliferation.
Figure 5:
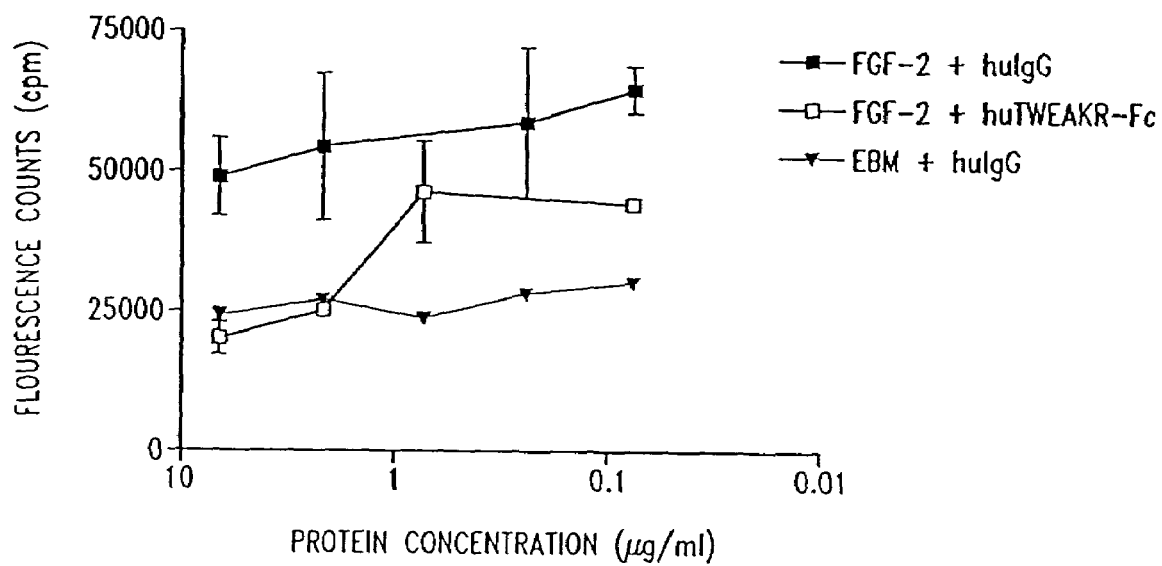
FIG. 5 shows the effect of human TWEAKR-Fc on FGF-2-induced (10 ng/ml) HUVEC proliferation.
Figure 6:
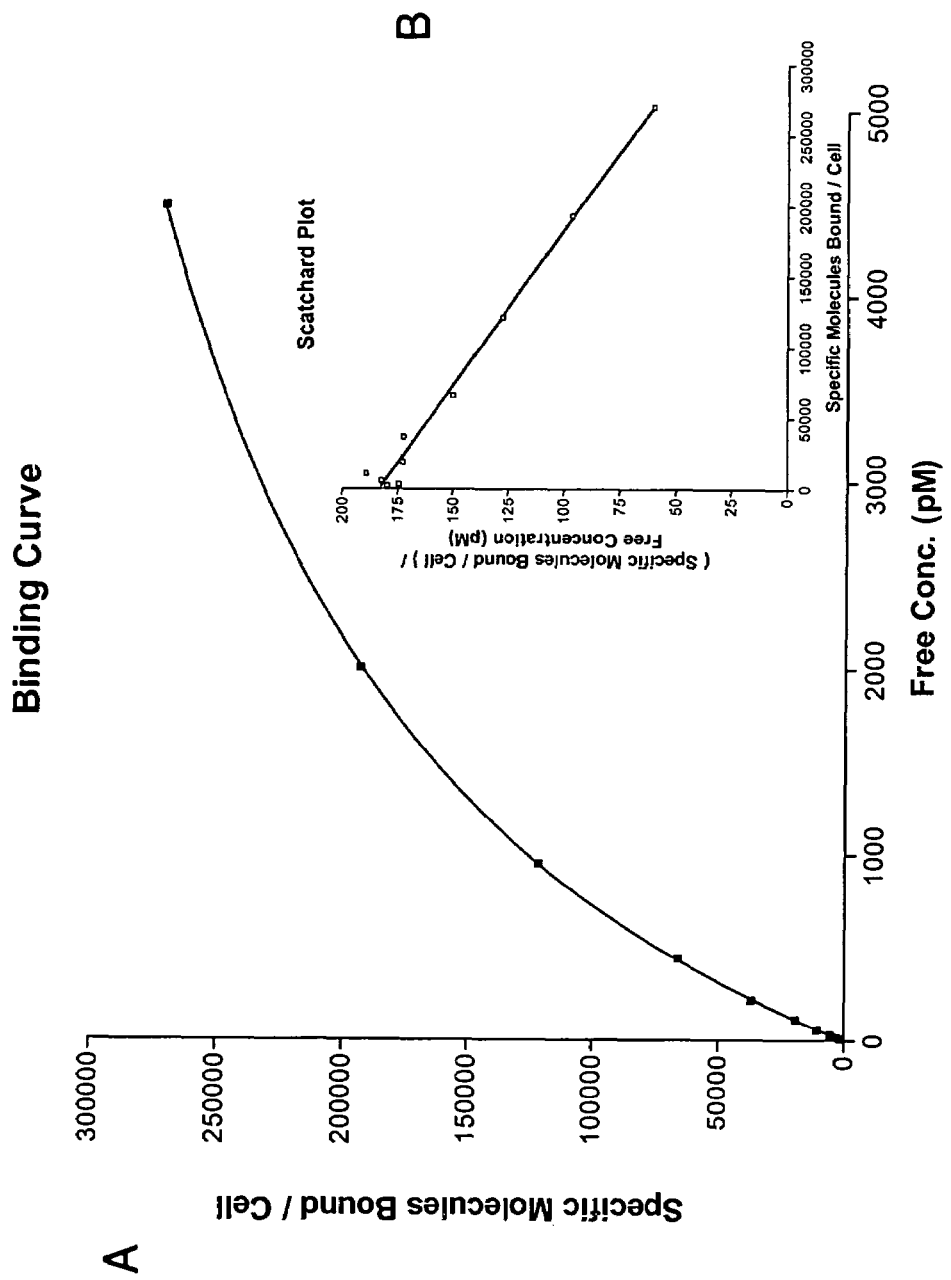
FIG. 6 collectively shows a scatchard analysis of TWEAK-TWEAKR interaction. CV-1 cells transfected with human full-length TWEAK mixed 1:30 with Raji cells and incubated with various concentrations of $^{125}$I-labeled TWEAKR-Fc. A) Shows scatchard representation of specific binding. B) Plot of competitive inhibition of unlabeled vs. $^{125}$I-labeled TWEAKR-Fc.
Figure 7A:
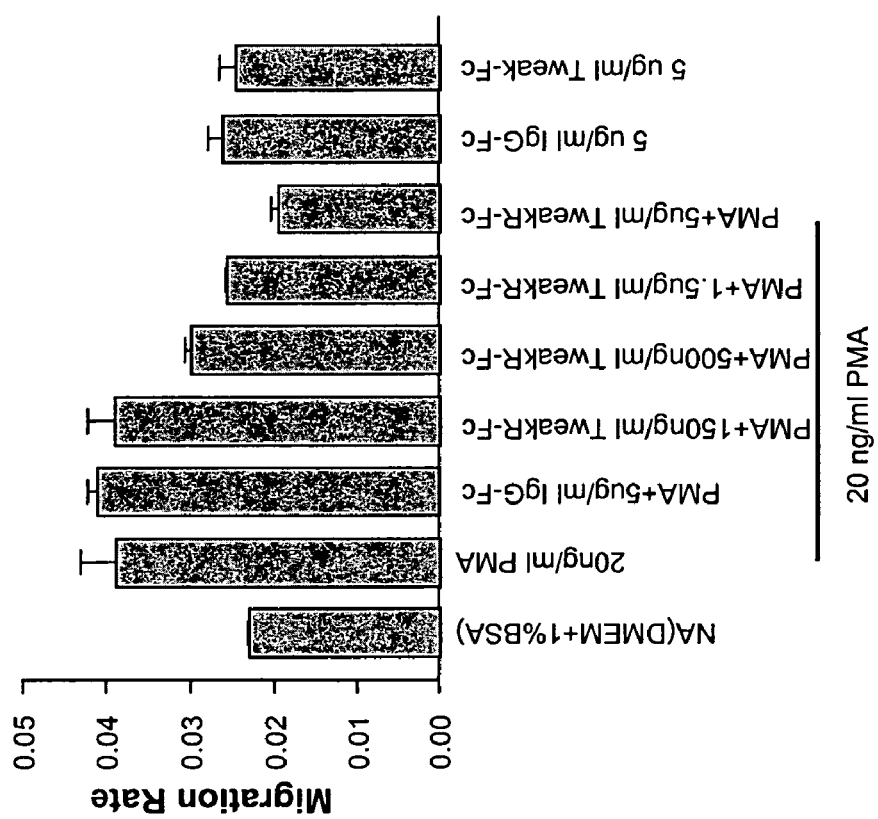
FIG. 7 collectively shows that human TWEAKR-Fc inhibits PMA- or EGF-stimulated endothelial cell migration in vitro. A, Shows that TWEAKR-Fc inhibited the PMA-stimulated migration rate to baseline at concentrations greater than or equal to 1.5 μg/ml, whereas huIgG at similar concentrations did not effect migration. Neither huIgG nor TweakR-Fc increased or decreased the basal migration rate when added to the cultures alone. B, Human TweakR-Fc inhibits EGF-induced endothelial cell migration. TweakR-Fc inhibited EGF-stimulated migration to basal levels at 5μg/ml. Partial inhibition of EGF-induced migration was also observed at huTweakR/Fc concentrations of 500 ng/ml and 1.5 μg/ml.
Figure 7B:
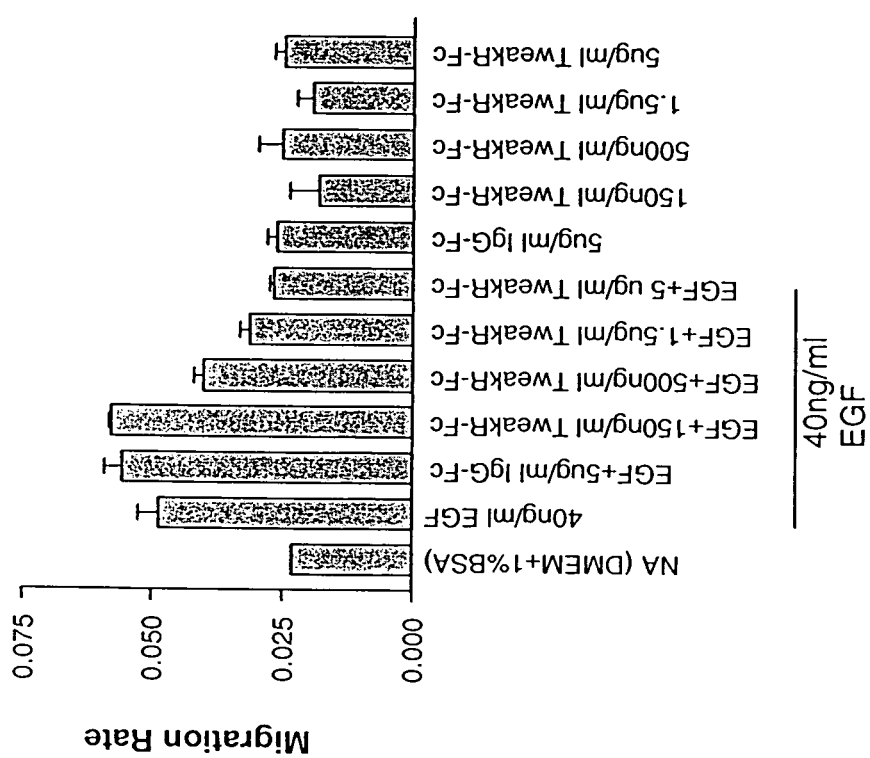

TWEAKR-Fc specifically inhibited TWEAK-induced HUVEC proliferation in a dose-dependent manner when compared to huIgG, which did not effect TWEAK-induced proliferation (FIG. 4). In addition, TWEAKR-Fc inhibited the basal proliferation of HUVEC observed during culture in EBM plus 0.05% FBS, as compared to huIgG, which did not. Interestingly, TWEAKR-Fc also inhibited FGF-2 mediated HUVEC proliferation at concentrations of greater than 2 µg/ml, as compared to huIgG, which did not effect the FGF-2 induced HUVEC proliferative response (FIG. 5). These results show that TWEAKR-Fc inhibits HUVEC proliferation induced by the addition of exogenous recombinant human TWEAK. That TWEAKR-Fc partially inhibits serum-induced HUVEC-proliferation indicates HUVEC produce endogenous TWEAK that promotes growth/survival of the EC (endothelial cell) via the TWEAKR. TWEAKR-Fc attenuation of FGF-2 induced proliferation indicates that at least part of the EC response to FGF-2 is dependent on endogenous TWEAK/TWEAKR interaction.

In another set of experiments to examine the effects of TWEAKR on proliferation of HUVEC cells a construct was made that fused a synthetic FLAG octapeptide epitope onto the N-terminal extracellular domain of TWEAKR (FLAG-TWEAKR). The resulting protein was expressed by transient transfection in HUVEC and incubated with cross-linked anti-FLAG monoclonal antibody. Cross-linking the receptor in this manner avoids background from the endogenous TWEAKR expressed by HUVEC. Proliferation was measured by BrdU uptake. Lipid mediated transfection of HUVEC with FLAG-TWEAKR resulted in expression of recombinant FLAG-TWEAKR on the cell surface by 36 hours post transfection. In vitro culture of FLAG-TWEAKR expressing HUVEC with the complex of M2 anti-FLAG and goat anti-mouse IgG increased BrdU incorporation 3-fold over the level of BrdU incorporation observed by culturing FLAG-TWEAKR expression cells with goat anti-mouse IgG alone. Cultures of FLAG-TWEAKR expressing HUVEC with the complex of M2 anti-FLAG and goat anti-IgG increased BrdU incorporation 6-fold over the level of BrdU incorporation observed by culturing vector-only transfected HUVEC with the cross-linking complex. Incubation with the cross-linking complex did not alter BrdU incorporation in vector alone transfected HUVEC. As an additional control, cells transfected with the FLAG construct that were not exposed to anti-FLAG also showed decreased BrdU uptake relative those that were exposed to crosslinked anti-FLAG. This data provides additional evidence that despite the small size of TWEAKR, TWEAKR is capable of initiating a proliferative signal in human endothelial cells.

Example 7

Inhibition of Neovascularization by TWEAKR-Fc in a Murine Transplant Model

Survival of heterotopically transplanted cardiac tissue from one mouse donor to the ear skin of another genetically similar mouse requires adequate neovascularization by the transplanted heart and the surrounding tissue, to promote survival and energy for cardiac muscle function. Inadequate vasculature at the site of transplant causes excessive ischemia to the heart, tissue damage, and failure of the tissue to engraft. Agents that antagonize the angiopoietins and endothelial specific factors involved in endothelial cell migration and vessel formation can decrease angiogenesis at the site of transplant, thereby limiting graft tissue function and ultimately engraftment itself.

The following studies were carried out, utilizing a murine heterotopic cardiac isograft model, in order to demonstrate the antagonistic effects of TWEAKR-Fc on neovascularization. In all experiments, female BALB/c (≈12 weeks of age) recipients received neonatal heart grafts from donor mice of the same strain.

TWEAKR-Fc Dose Titration

In the described experiments, the donor heart tissue was engrafted into the left ear pinnae of the recipient on day 0 and the mice were divided into treatment groups. The control group received human IgG (Hu IgG, 400 µg/day) while the other treatment groups human TWEAKR-Fc at a dose of 400 µg/day or 150 µg/day. All treatments (proteins administered by intraperitoneal injection) began on day 0 and continued for four consecutive days. The functionality of the grafts was determined by monitoring visible pulsatile activity on days 7 and 12 post-engraftment. Table 2 shows the experimental results.

TABLE 2

Functional Heart Isoengraftment Following Dose Titration with TweakR/Fc

| Treatment | Day 7 | Day 12 | N= |
|---|---|---|---|
| Hu IgG 400 µg | 100* | 100 | 3 |
| HuTWEAKR-Fc 150 µg | 100 | 100 | 5 |
| HuTWEAKR-Fc 400 µg | 40 | 80 | 5 |

*all results are reported as percent of mice with pulsatile heart grafts

Administration of TWEAKR-Fc to isograft-bearing mice caused a significant, dose-dependent, delay in cardiac isoengraftment. Sixty percent of TWEAKR-Fc-treated mice at the 400ug/day dose, failed to exhibit pulsatile activity on day 7 post transplant as compared to huIgG control, where no effect on isoengraftment was observed. At this dose, TWEAKkR-Fc administration caused permanent engraftment failure in one fifth of the mice compared to huIgG control where no effect on engraftment was observed. While a dose of 400 µg of huTWEAKR-Fc showed a significant anti-angiogenic effect, a 150 µg dose of TWEAKR-Fc did not show measurable activity in this model.

Example 8

Regulation of TWEAKR mRNA Expression I Vascular Smooth Muscle Cells (SMC)

Rat aortic SMC were serum-starved and then treated with FGF for various lengths of time. RNA was isolated and TWEAKR mRNA levels were examined by Northern Blot hybridization. A single TWEAKR transcript of ≈1.2 kb in size was detected in SMC. TWEAKR MRNA expression was transiently induced following FGF addition, with maximal levels detected at 2 hours post stimulation. Serum-starved SMC were also treated for 4 hours with various agents (e.g., phorbol ester, polypeptide growth factors, peptide hormones) and then a Northern blot was performed to determine whether TWEAKR gene expression could be induced by multiple distinct growth promoters. TWEAKR mRNA levels were significantly elevated following PMA, FBS, PDGF-BB, EGF, FGF or Ang II treatment of rat SMC. TGF-beta1, IGF-1 and alpha-thrombin treatment had only a slight stimulatory effect. These results indicate that WEAKR is a growth factor-regulated gene in vascular SMC.

Example 9

Chromosome Mapping

The gene corresponding to a TWEAKR polypeptide is mapped using PCR-based mapping strategies. Initial human chromosomal assignments are made using TWEAKR-specific PCR primers and a BIOS Somatic Cell Hybrid PCRable DNA kit from BIOS Laboratories (New Haven, Conn.), following the manufacturer's instructions. More detailed mapping is performed using a Genebridge 4 Radiation Hybrid Panel (Research Genetics, Huntsville, Ala.; described in Walter et al., *Nature Genetics* 7:22-28, 1994). Data from this analysis is then submitted electronically to the MIT Radiation Hybrid Mapper following the instructions contained therein. This analysis yields specific genetic marker names which, when submitted electronically to the NCBI Genemap browser, yield the specific chromosome interval.

Example 10

TWEAKR Stability

Ligand blots were generated by running either TweakR-Fc or RP-Fc as a control on a standard SDS-PAGE and blotted onto nitrocellulose. The separate samples were prepared by with and without the addition of reducing agent (DTT) and with and without heating at 100° C. to denature the proteins. This blot was probed with TWEAK-leucine zipper conditioned supernatants followed by $^{125}$I, labeled M15 anti-leucine zipper. The results showed that all TweakR-FC samples strongly bound TWEAK while the RP-Fc samples did not. This shows that TweakR ligand binding domain will spontaneously refold into an active conformation even after begin reduced and boiled in SDS loading buffer.

Example 11

Treatment of Tumors with TWEAKR Antagonists

TWEAKR antagonists, including antibodies and TWEAKR-Fc, are tested in animal models of solid tumors. The effect of the TWEAKR antagonists is determined by measuring tumor frequency and tumor growth.

The relevant disclosures of publications cited herein are specifically incorporated by reference. The examples presented above are not intended to be exhaustive or to limit the scope of the invention. The skilled artisan will understand that variations and modifications and variations are possible in light of the above teachings, and such modifications and variations are intended to be within the scope of the invention.

What is claimed is:

1. An isolated monoclonal antibody, wherein said antibody binds to a polypeptide consisting of residues 28 to 68 of SEQ ID NO:4, binds to the extracellular domain of a human TWEAK receptor consisting of the amino acid sequence of SEQ ID NO:4, and inhibits binding of a TWEAK molecule to said TWEAK receptor.

2. The isolated monoclonal antibody of claim 1, wherein said antibody binds to the cysteine-rich repeat region of said TWEAK receptor.

3. The isolated monoclonal antibody of claim 1, wherein said antibody inhibits angiogenesis.

4. The isolated monoclonal antibody of claim 1, wherein said antibody promotes angiogenesis.

5. The isolated monoclonal antibody of claim 1, wherein said human TWEAK receptor is glycosylated.

6. The isolated monoclonal antibody of claim 1, wherein said antibody comprises a radioisotope, a plant-derived toxin, a fungus-derived toxin, a bacterial-derived toxin, ricin A, or diphtheria toxin.

7. The isolated antibody of claim 1, wherein said antibody comprises a detectable label.

8. The isolated antibody of claim 7, wherein said detectable label comprises a radioisotope, a chemiluminescent compound, a fluorescent compound, or an enzyme.

9. The isolated monoclonal antibody of claim 1, wherein said antibody is selected from the group consisting of:
   a) an intact human antibody;
   b) a human antibody fragment;
   c) an intact chimeric antibody;
   d) a chimeric antibody fragment;
   e) an intact humanized antibody;
   f) a humanized antibody fragment;
   g) a Fab fragment;
   h) an Fv fragment;
   i) an F(ab')2 fragment; and
   j) a single chain antibody.

10. An isolated polypeptide, wherein said polypeptide comprises the monoclonal antibody of claim 1 and inhibits binding of a TWEAK molecule to said TWEAK receptor.

11. An isolated cell, wherein said cell produces the monoclonal antibody of claim 1.

12. An isolated cell, wherein said cell produces the polypeptide of claim 10.

13. The isolated cell of claim 11, wherein said cell is a hybridoma.

14. The isolated cell of claim 11, wherein said cell is a recombinant cell.

15. The isolated cell of claim 12, wherein said cell is a recombinant cell.

16. A method of inhibiting binding of TWEAK to a TWEAK receptor in a subject in need of such treatment comprising administering to said subject an inhibition-effective amount of said antibody of claim 1.

17. The method of claim 16 wherein said subject is a human.

18. The method of claim 16 wherein the subject has a disease or condition mediated by angiogenesis.

19. The method of claim 18 wherein the disease or condition is characterized by ocular neovascularization.

20. The method of claim 18 wherein the disease or condition is a malignant or metastatic condition.

21. The method of claim 20 wherein the malignant or metastatic condition is a solid tumor.

22. The method of claim 20 wherein the method further comprises treating the subject with radiation.

23. The method of claim 20 wherein the method further comprises treating the subject with a second chemotherapeutic agent.

24. The method of claim 23 wherein the second chemotherapeutic agent is selected from the group consisting of alkylating agents, antimetabolites, vinca alkaloids and other plant-derived chemotherapeutics, nitrosoureas, antitumor antibiotics, antitumor enzymes, topoisomerase inhibitors, platinum analogs, adrenocortical suppressants, hormones, hormone agonists, hormone antagonists, antibodies, immunotherapeutics, blood cell factors, radiotherapeutics, and biological response modifiers.

25. The method of claim 23 wherein the second chemotherapeutic agent is selected from the group consisting of cisplatin, cyclophosphamide, mechloretamine, melphalan, bleomycin, carboplatin, fluorouracil, 5 -fluorodeoxyuridine, methotrexate, taxol, asparaginase, vincristine, and vinblastine, lymphokines, cytokines, interleukins, interferons, alpha interferon, beta interferon, delta interferon, TNF, chlorambucil, busulfan, carmustine, lomustine, semustine, streptozocin, dacarbazine, cytarabine, mercaptopurine, thioguanine, vindesine, etoposide, teniposide, dactinomycin, daunorubicin, doxorubicin, plicamycin, mitomycin, L-asparaginase, hydroxyurea, methylhydrazine, mitotane, tamoxifen, and fluoxymesterone.

26. The method of claim 23 wherein the second chemotherapeutic agent is selected from the group consisting of Flt3 ligand, CD40 ligand, interleukin-2, interleukin-12, 4-1BB ligand, anti-4-1BB antibodies, TNF antagonists and TNF receptor antagonists, TRAIL, CD148 agonists, VEGF antagonists, VEGF receptor antagonists, and Tek antagonists.

27. A method of inhibiting binding of TWEAK to a TWEAK receptor in a subject in need of such treatment comprising administering to said subject an inhibition-effective amount of said polypeptide of claim 10.

28. The method of claim 27 wherein said subject is a human.

29. The method of claim 27 wherein the subject has a disease or condition mediated by angiogenesis.

30. The method of claim 29 wherein the disease or condition is characterized by ocular neovascularization.

31. The method of claim 29 wherein the disease or condition is a malignant or metastatic condition.

32. The method of claim 31 wherein the malignant or metastatic condition is a solid tumor.

33. The method of claim 31 wherein the method further comprises treating the subject with radiation.

34. The method of claim 31 wherein the method further comprises treating the subject with a second chemotherapeutic agent.

35. The method of claim 34 wherein the second chemotherapeutic agent is selected from the group consisting of alkylating agents, antimetabolites, vinca alkaloids and other plant-derived chemotherapeutics, mitrosoureas, antitumor antibiotics, antitumor enzymes, topoisomerase inhibitors, platinum analogs, adrenocortical suppressants, hormones, hormone agonists, hormone antagonists, antibodies, immunotherapeutics, blood cell factors, radiotherapeutics, and biological response modifiers.

36. The method of claim 34 wherein the second chemotherapeutic agent is selected from the group consisting of cisplatin, cyclophosphamide, mechloretamine, melphalan, bleomycin, carboplatin, fluorouracil, 5-fluorodeoxyuridine, methotrexate, taxol, asparaginase, vincritine, and vinblastine, lymphokkines, cytokines, interleukins, interferons, alpha interferon, beta interferon, delta interferon, TNF, chlorambucil, busulfan, carmustine, lomustine, semustine, streptozocin, dacarbazine, cytarabine, mercaptopurine, thioguanine, vindesine, etoposide, teniposide, dactinomycin, daunorubicin, doxorubicin, plicamycin, mitomycin, L-asparaginase, hydroxyurea, methylhydrazine, mitotane, tamoxifen, and fluoxymesterone.

37. The method of claim 34 wherein the second chemotherapeutic agent is selected from the group consisting of Flt3 ligand, CD40 ligand, interleukin-2, interleukin-12, 4-1BB ligand, anti-4-BB antibodies, TNF antagonists and TNF receptor antagonists, TRAIL, CD148 agonists, VEGF antagonists, VEGF receptor antagonists, and Tek antagonists.

\* \* \* \* \*

SEQUENCE LISTING

```
<160> NUMBER OF SEQ ID NOS: 16

<210> SEQ ID NO 1
<211> LENGTH: 898
<212> TYPE: DNA
<213> ORGANISM: Artificial sequence
<220> FEATURE:
<223> OTHER INFORMATION: TWEAK fusion protein construct
<220> FEATURE:
<221> NAME/KEY: CDS
<222> LOCATION: (52)..(873)
<223> OTHER INFORMATION:

<400> SEQUENCE: 1
tctcgagggc cacgcgttta aacgtcgagg tacctatccc gggccgccac c atg gct        57
                                                         Met Ala
                                                         1 aca ggc tcc cgg acg tcc ctg ctc ctg gct ttt ggc ctg ctc tgc ctg       105
Thr Gly Ser Arg Thr Ser Leu Leu Leu Ala Phe Gly Leu Leu Cys Leu
         5                  10                  15 ccc tgg ctt caa gag ggc agt gca act agt tct gac cgt atg aaa cag       153
Pro Trp Leu Gln Glu Gly Ser Ala Thr Ser Ser Asp Arg Met Lys Gln
    20                  25                  30 ata gag gat aag atc gaa gag atc cta agt aag att tat cat ata gag       201
Ile Glu Asp Lys Ile Glu Glu Ile Leu Ser Lys Ile Tyr His Ile Glu
35                  40                  45                  50 aat gaa atc gcc cgt atc aaa aag ctg att ggc gag cgg act aga tct       249
Asn Glu Ile Ala Arg Ile Lys Lys Leu Ile Gly Glu Arg Thr Arg Ser
                55                  60                  65 agt ttg ggg agc cgg gca tcg ctg tcc gcc cag gag cct gcc cag gag       297
Ser Leu Gly Ser Arg Ala Ser Leu Ser Ala Gln Glu Pro Ala Gln Glu
            70                  75                  80
```

```
gag ctg gtg gca gag gag gac cag gac ccg tcg gaa ctg aat ccc cag        345
Glu Leu Val Ala Glu Glu Asp Gln Asp Pro Ser Glu Leu Asn Pro Gln
        85                  90                  95 aca gaa gaa agc cag gat cct gcg cct ttc ctg aac cga cta gtt cgg        393
Thr Glu Glu Ser Gln Asp Pro Ala Pro Phe Leu Asn Arg Leu Val Arg
100                 105                 110 cct cgc aga agt gca cct aaa ggc cgg aaa aca cgg gct cga aga gcg        441
Pro Arg Arg Ser Ala Pro Lys Gly Arg Lys Thr Arg Ala Arg Arg Ala
    115                 120                 125             130 atc gca gcc cat tat gaa gtt cat cca cga cct gga cag gac gga gcg        489
Ile Ala Ala His Tyr Glu Val His Pro Arg Pro Gly Gln Asp Gly Ala
                135                 140                 145 cag gca ggt gtg gac ggg aca gtg agt ggc tgg gag gaa gcc aga atc        537
Gln Ala Gly Val Asp Gly Thr Val Ser Gly Trp Glu Glu Ala Arg Ile
                150                 155                 160 aac agc tcc agc cct ctg cgc tac aac cgc cag atc ggg gag ttt ata        585
Asn Ser Ser Ser Pro Leu Arg Tyr Asn Arg Gln Ile Gly Glu Phe Ile
                165                 170                 175 gtc acc cgg gct ggg ctc tac tac ctg tac tgt cag gtg cac ttt gat        633
Val Thr Arg Ala Gly Leu Tyr Tyr Leu Tyr Cys Gln Val His Phe Asp
180                 185                 190 gag ggg aag gct gtc tac ctg aag ctg gac ttg ctg gtg gat ggt gtg        681
Glu Gly Lys Ala Val Tyr Leu Lys Leu Asp Leu Leu Val Asp Gly Val
195                 200                 205                 210 ctg gcc ctg cgc tgc ctg gag gaa ttc tca gcc act gcg gcc agt tcc        729
Leu Ala Leu Arg Cys Leu Glu Glu Phe Ser Ala Thr Ala Ala Ser Ser
            215                 220                 225 ctc ggg ccc cag ctc cgc ctc tgc cag gtg tct ggg ctg ttg gcc ctg        777
Leu Gly Pro Gln Leu Arg Leu Cys Gln Val Ser Gly Leu Leu Ala Leu
                230                 235                 240 cgg cca ggg tcc tcc ctg cgg atc cgc acc ctc ccc tgg gcc cat ctc        825
Arg Pro Gly Ser Ser Leu Arg Ile Arg Thr Leu Pro Trp Ala His Leu
                245                 250                 255 aag gct gcc ccc ttc ctc acc tac ttc gga ctc ttc cag gtt cac tga        873
Lys Ala Ala Pro Phe Leu Thr Tyr Phe Gly Leu Phe Gln Val His
260                 265                 270 gcggccgcgg atctgtttaa actag                                            898

<210> SEQ ID NO 2
<211> LENGTH: 273
<212> TYPE: PRT
<213> ORGANISM: Artificial sequence
<220> FEATURE:
<223> OTHER INFORMATION: TWEAK fusion protein construct

<400> SEQUENCE: 2

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Thr Ser Ser Asp Arg Met
                20                  25                  30

Lys Gln Ile Glu Asp Lys Ile Glu Glu Ile Leu Ser Lys Ile Tyr His
            35                  40                  45

Ile Glu Asn Glu Ile Ala Arg Ile Lys Lys Leu Ile Gly Glu Arg Thr
        50                  55                  60

Arg Ser Ser Leu Gly Ser Arg Ala Ser Leu Ala Gln Glu Pro Ala
65                  70                  75                  80

Gln Glu Glu Leu Val Ala Glu Glu Asp Gln Asp Pro Ser Glu Leu Asn
                85                  90                  95
```

```
Pro Gln Thr Glu Glu Ser Gln Asp Pro Ala Pro Phe Leu Asn Arg Leu
            100                 105                 110

Val Arg Pro Arg Arg Ser Ala Pro Lys Gly Arg Lys Thr Arg Ala Arg
        115                 120                 125

Arg Ala Ile Ala Ala His Tyr Glu Val His Pro Arg Pro Gly Gln Asp
    130                 135                 140

Gly Ala Gln Ala Gly Val Asp Gly Thr Val Ser Gly Trp Glu Glu Ala
145                 150                 155                 160

Arg Ile Asn Ser Ser Ser Pro Leu Arg Tyr Asn Arg Gln Ile Gly Glu
                165                 170                 175

Phe Ile Val Thr Arg Ala Gly Leu Tyr Tyr Leu Tyr Cys Gln Val His
            180                 185                 190

Phe Asp Glu Gly Lys Ala Val Tyr Leu Lys Leu Asp Leu Leu Val Asp
        195                 200                 205

Gly Val Leu Ala Leu Arg Cys Leu Glu Glu Phe Ser Ala Thr Ala Ala
    210                 215                 220

Ser Ser Leu Gly Pro Gln Leu Arg Leu Cys Gln Val Ser Gly Leu Leu
225                 230                 235                 240

Ala Leu Arg Pro Gly Ser Ser Leu Arg Ile Arg Thr Leu Pro Trp Ala
                245                 250                 255

His Leu Lys Ala Ala Pro Phe Leu Thr Tyr Phe Gly Leu Phe Gln Val
            260                 265                 270

His

<210> SEQ ID NO 3
<211> LENGTH: 868
<212> TYPE: DNA
<213> ORGANISM: homo sapiens
<220> FEATURE:
<221> NAME/KEY: CDS
<222> LOCATION: (53)..(442)
<223> OTHER INFORMATION:

<400> SEQUENCE: 3
gcttgaattc aataactata acggtcctaa ggtagcgaag aggacgtgca ct atg gct     58
                                                         Met Ala
                                                           1 cgg ggc tcg ctg cgc cgg ttg ctg cgg ctc ctc gtg ctg ggc ctc tgg    106
Arg Gly Ser Leu Arg Arg Leu Leu Arg Leu Leu Val Leu Gly Leu Trp
        5                   10                  15 ctg gcg ttg ctg cgc tcc gtg gcc ggg gag caa gcg cca ggc acc gcc    154
Leu Ala Leu Leu Arg Ser Val Ala Gly Glu Gln Ala Pro Gly Thr Ala
    20                  25                  30 ccc tgc tcc cgc ggc agc tcc tgg agc gcg gac ctg gac aag tgc atg    202
Pro Cys Ser Arg Gly Ser Ser Trp Ser Ala Asp Leu Asp Lys Cys Met
35                  40                  45                  50 gac tgc gcg tct tgc agg gcg cga ccg cac agc gac ttc tgc ctg ggc    250
Asp Cys Ala Ser Cys Arg Ala Arg Pro His Ser Asp Phe Cys Leu Gly
                55                  60                  65 tgc gct gca gca cct cct gcc ccc ttc cgg ctg ctt tgg ccc atc ctt    298
Cys Ala Ala Ala Pro Pro Ala Pro Phe Arg Leu Leu Trp Pro Ile Leu
            70                  75                  80 ggg ggc gct ctg agc ctg acc ttc gtg ctg ggg ctg ctt tct ggc ttt    346
Gly Gly Ala Leu Ser Leu Thr Phe Val Leu Gly Leu Leu Ser Gly Phe
        85                  90                  95 ttg gtc tgg aga cga tgc cgc agg aga gag aag ttc acc acc ccc ata    394
Leu Val Trp Arg Arg Cys Arg Arg Arg Glu Lys Phe Thr Thr Pro Ile
    100                 105                 110
```

-continued

```
gag gag acc ggc gga gag ggc tgc cca gct gtg gcg ctg atc cag tga    442
Glu Glu Thr Gly Gly Glu Gly Cys Pro Ala Val Ala Leu Ile Gln
115                 120                 125 caatgtgccc cctgccagcc ggggctcgcc cactcatcat tcattcatcc attctagagc    502
cagtctctgc ctcccagacg cggcgggagc caagctcctc caaccacaag ggggtgggg     562 ggcggtgaat cacctctgag cctgggccc agggttcagg ggaaccttcc aaggtgtctg     622
gttgccctgc ctctggctcc agaacagaaa gggagcctca cgctggctca cacaaaacag    682
ctgacactga ctaaggaact gcagcatttg cacaggggag gggggtgccc tccttcctag    742
aggccctggg ggccaggctg acttgggggg cagacttgac actaggcccc actcactcag    802
atgtcctgaa attccaccac gggggtcacc ctgggggtt agggacctat ttttaacact     862
agaggg                                                                868
```

<210> SEQ ID NO 4
<211> LENGTH: 129
<212> TYPE: PRT
<213> ORGANISM: homo sapiens

<400> SEQUENCE: 4

```
Met Ala Arg Gly Ser Leu Arg Arg Leu Leu Arg Leu Val Leu Gly
1               5                   10                  15

Leu Trp Leu Ala Leu Leu Arg Ser Val Ala Gly Glu Gln Ala Pro Gly
                20                  25                  30

Thr Ala Pro Cys Ser Arg Gly Ser Ser Trp Ser Ala Asp Leu Asp Lys
                35                  40                  45

Cys Met Asp Cys Ala Ser Cys Arg Ala Arg Pro His Ser Asp Phe Cys
        50                  55                  60

Leu Gly Cys Ala Ala Ala Pro Pro Ala Pro Phe Arg Leu Leu Trp Pro
65                  70                  75                  80

Ile Leu Gly Gly Ala Leu Ser Leu Thr Phe Val Leu Gly Leu Leu Ser
                85                  90                  95

Gly Phe Leu Val Trp Arg Arg Cys Arg Arg Arg Glu Lys Phe Thr Thr
                100                 105                 110

Pro Ile Glu Glu Thr Gly Gly Glu Gly Cys Pro Ala Val Ala Leu Ile
            115                 120                 125

Gln
```

<210> SEQ ID NO 5
<211> LENGTH: 129
<212> TYPE: PRT
<213> ORGANISM: Mus sp.

<400> SEQUENCE: 5

```
Met Ala Pro Gly Trp Pro Arg Ser Leu Pro Gln Ile Leu Val Leu Gly
1               5                   10                  15

Phe Gly Leu Val Leu Met Arg Ala Ala Ala Gly Glu Gln Ala Pro Gly
                20                  25                  30

Thr Ser Pro Cys Ser Ser Gly Ser Ser Trp Ser Ala Asp Leu Asp Lys
                35                  40                  45

Cys Met Asp Cys Ala Ser Cys Pro Ala Arg Pro His Ser Asp Phe Cys
        50                  55                  60

Leu Gly Cys Ala Ala Ala Pro Pro Ala His Phe Arg Leu Leu Trp Pro
65                  70                  75                  80

Ile Leu Gly Gly Ala Leu Ser Leu Val Leu Val Leu Ala Leu Val Ser
                85                  90                  95
```

```
Ser Phe Leu Val Trp Arg Arg Cys Arg Arg Glu Lys Phe Thr Thr
                100                 105                 110

Pro Ile Glu Glu Thr Gly Gly Glu Gly Cys Pro Gly Val Ala Leu Ile
        115                 120                 125

Gln

<210> SEQ ID NO 6
<211> LENGTH: 932
<212> TYPE: DNA
<213> ORGANISM: Artificial Sequence
<220> FEATURE:
<223> OTHER INFORMATION: Human TWEAK receptor fusion protein construct
<220> FEATURE:
<221> NAME/KEY: CDS
<222> LOCATION: (1)..(930)
<223> OTHER INFORMATION:

<400> SEQUENCE: 6
```

| | | | | | | | | | | | | | | | | |
|---|---|---|---|---|---|---|---|---|---|---|---|---|---|---|---|---|
| atg | gct | cgg | ggc | tcg | ctg | cgc | cgg | ttg | ctg | cgg | ctc | ctc | gtg | ctg | ggg | 48 |
| Met | Ala | Arg | Gly | Ser | Leu | Arg | Arg | Leu | Leu | Arg | Leu | Leu | Val | Leu | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ctc | tgg | ctg | gcg | ttg | ctg | cgc | tcc | gtg | gcc | ggg | gag | caa | gcg | cca | ggc | 96 |
| Leu | Trp | Leu | Ala | Leu | Leu | Arg | Ser | Val | Ala | Gly | Glu | Gln | Ala | Pro | Gly | |
| | | | 20 | | | | | 25 | | | | | 30 | | | |

| | | | | | | | | | | | | | | | | |
|---|---|---|---|---|---|---|---|---|---|---|---|---|---|---|---|---|
| acc | gcc | ccc | tgc | tcc | cgc | ggc | agc | tcc | tgg | agc | gcg | gac | ctg | gac | aag | 144 |
| Thr | Ala | Pro | Cys | Ser | Arg | Gly | Ser | Ser | Trp | Ser | Ala | Asp | Leu | Asp | Lys | |
| | | 35 | | | | | 40 | | | | | 45 | | | | |

| | | | | | | | | | | | | | | | | |
|---|---|---|---|---|---|---|---|---|---|---|---|---|---|---|---|---|
| tgc | atg | gac | tgc | gcg | tct | tgc | agg | gcg | cga | ccg | cac | agc | gac | ttc | tgc | 192 |
| Cys | Met | Asp | Cys | Ala | Ser | Cys | Arg | Ala | Arg | Pro | His | Ser | Asp | Phe | Cys | |
| | 50 | | | | | 55 | | | | | 60 | | | | | |

| | | | | | | | | | | | | | | | | |
|---|---|---|---|---|---|---|---|---|---|---|---|---|---|---|---|---|
| ctg | ggc | tgc | gct | gca | gca | cct | cct | gcc | ccc | ttc | cgg | ctg | ctt | tgg | aga | 240 |
| Leu | Gly | Cys | Ala | Ala | Ala | Pro | Pro | Ala | Pro | Phe | Arg | Leu | Leu | Trp | Arg | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| tct | tgt | gac | aaa | act | cac | aca | tgc | cca | ccg | tgc | cca | gca | cct | gaa | gcc | 288 |
| Ser | Cys | Asp | Lys | Thr | His | Thr | Cys | Pro | Pro | Cys | Pro | Ala | Pro | Glu | Ala | |
| | | | | 85 | | | | | 90 | | | | | 95 | | |

| | | | | | | | | | | | | | | | | |
|---|---|---|---|---|---|---|---|---|---|---|---|---|---|---|---|---|
| gag | ggc | gcg | ccg | tca | gtc | ttc | ctc | ttc | ccc | cca | aaa | ccc | aag | gac | acc | 336 |
| Glu | Gly | Ala | Pro | Ser | Val | Phe | Leu | Phe | Pro | Pro | Lys | Pro | Lys | Asp | Thr | |
| | | | 100 | | | | | 105 | | | | | 110 | | | |

| | | | | | | | | | | | | | | | | |
|---|---|---|---|---|---|---|---|---|---|---|---|---|---|---|---|---|
| ctc | atg | atc | tcc | cgg | acc | cct | gag | gtc | aca | tgc | gtg | gtg | gtg | gac | gtg | 384 |
| Leu | Met | Ile | Ser | Arg | Thr | Pro | Glu | Val | Thr | Cys | Val | Val | Val | Asp | Val | |
| | | | 115 | | | | | 120 | | | | | 125 | | | |

| | | | | | | | | | | | | | | | | |
|---|---|---|---|---|---|---|---|---|---|---|---|---|---|---|---|---|
| agc | cac | gaa | gac | cct | gag | gtc | aag | ttc | aac | tgg | tac | gtg | gac | ggc | gtg | 432 |
| Ser | His | Glu | Asp | Pro | Glu | Val | Lys | Phe | Asn | Trp | Tyr | Val | Asp | Gly | Val | |
| | 130 | | | | | 135 | | | | | 140 | | | | | |

| | | | | | | | | | | | | | | | | |
|---|---|---|---|---|---|---|---|---|---|---|---|---|---|---|---|---|
| gag | gtg | cat | aat | gcc | aag | aca | aag | ccg | cgg | gag | gag | cag | tac | aac | agc | 480 |
| Glu | Val | His | Asn | Ala | Lys | Thr | Lys | Pro | Arg | Glu | Glu | Gln | Tyr | Asn | Ser | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| acg | tac | cgt | gtg | gtc | agc | gtc | ctc | acc | gtc | ctg | cac | cag | gac | tgg | ctg | 528 |
| Thr | Tyr | Arg | Val | Val | Ser | Val | Leu | Thr | Val | Leu | His | Gln | Asp | Trp | Leu | |
| | | | 165 | | | | | 170 | | | | | 175 | | | |

| | | | | | | | | | | | | | | | | |
|---|---|---|---|---|---|---|---|---|---|---|---|---|---|---|---|---|
| aat | ggc | aag | gag | tac | aag | tgc | aag | gtc | tcc | aac | aaa | gcc | ctc | cca | gcc | 576 |
| Asn | Gly | Lys | Glu | Tyr | Lys | Cys | Lys | Val | Ser | Asn | Lys | Ala | Leu | Pro | Ala | |
| | | | 180 | | | | | 185 | | | | | 190 | | | |

| | | | | | | | | | | | | | | | | |
|---|---|---|---|---|---|---|---|---|---|---|---|---|---|---|---|---|
| ccc | atc | gag | aaa | acc | atc | tcc | aaa | gcc | aaa | ggg | cag | ccc | cga | gaa | cca | 624 |
| Pro | Ile | Glu | Lys | Thr | Ile | Ser | Lys | Ala | Lys | Gly | Gln | Pro | Arg | Glu | Pro | |
| | | 195 | | | | | 200 | | | | | 205 | | | | |

| | | | | | | | | | | | | | | | | |
|---|---|---|---|---|---|---|---|---|---|---|---|---|---|---|---|---|
| cag | gtg | tac | acc | ctg | ccc | cca | tcc | cgg | gag | gag | atg | acc | aag | aac | cag | 672 |
| Gln | Val | Tyr | Thr | Leu | Pro | Pro | Ser | Arg | Glu | Glu | Met | Thr | Lys | Asn | Gln | |
| | 210 | | | | | 215 | | | | | 220 | | | | | |

-continued

```
gtc agc ctg acc tgc ctg gtc aaa ggc ttc tat ccc agc gac atc gcc      720
Val Ser Leu Thr Cys Leu Val Lys Gly Phe Tyr Pro Ser Asp Ile Ala
225                 230                 235                 240 gtg gag tgg gag agc aat ggg cag ccg gag aac aac tac aag acc acg      768
Val Glu Trp Glu Ser Asn Gly Gln Pro Glu Asn Asn Tyr Lys Thr Thr
                245                 250                 255 cct ccc gtg ctg gac tcc gac ggc tcc ttc ttc ctc tat agc aag ctc      816
Pro Pro Val Leu Asp Ser Asp Gly Ser Phe Phe Leu Tyr Ser Lys Leu
            260                 265                 270 acc gtg gac aag agc agg tgg cag cag ggg aac gtc ttc tca tgc tcc      864
Thr Val Asp Lys Ser Arg Trp Gln Gln Gly Asn Val Phe Ser Cys Ser
        275                 280                 285 gtg atg cat gag gct ctg cac aac cac tac acg cag aag agc ctc tcc      912
Val Met His Glu Ala Leu His Asn His Tyr Thr Gln Lys Ser Leu Ser
    290                 295                 300 ctg tct ccg ggt aaa tga ac                                           932
Leu Ser Pro Gly Lys
305
```

<210> SEQ ID NO 7
<211> LENGTH: 309
<212> TYPE: PRT
<213> ORGANISM: Artificial Sequence
<220> FEATURE:
<223> OTHER INFORMATION: Human TWEAK receptor fusion protein construct

<400> SEQUENCE: 7

```
Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
                20                  25                  30

Thr Ala Pro Cys Ser Arg Gly Ser Ser Trp Ser Ala Asp Leu Asp Lys
            35                  40                  45

Cys Met Asp Cys Ala Ser Cys Arg Ala Arg Pro His Ser Asp Phe Cys
        50                  55                  60

Leu Gly Cys Ala Ala Ala Pro Pro Ala Pro Phe Arg Leu Leu Trp Arg
65                  70                  75                  80

Ser Cys Asp Lys Thr His Thr Cys Pro Pro Cys Pro Ala Pro Glu Ala
                85                  90                  95

Glu Gly Ala Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125

Ser His Glu Asp Pro Glu Val Lys Phe Asn Trp Tyr Val Asp Gly Val
    130                 135                 140

Glu Val His Asn Ala Lys Thr Lys Pro Arg Glu Glu Gln Tyr Asn Ser
145                 150                 155                 160

Thr Tyr Arg Val Val Ser Val Leu Thr Val Leu His Gln Asp Trp Leu
                165                 170                 175

Asn Gly Lys Glu Tyr Lys Cys Lys Val Ser Asn Lys Ala Leu Pro Ala
            180                 185                 190

Pro Ile Glu Lys Thr Ile Ser Lys Ala Lys Gly Gln Pro Arg Glu Pro
        195                 200                 205

Gln Val Tyr Thr Leu Pro Pro Ser Arg Glu Glu Met Thr Lys Asn Gln
    210                 215                 220

Val Ser Leu Thr Cys Leu Val Lys Gly Phe Tyr Pro Ser Asp Ile Ala
225                 230                 235                 240
```

```
Val Glu Trp Glu Ser Asn Gly Gln Pro Glu Asn Asn Tyr Lys Thr Thr
                245                 250                 255

Pro Pro Val Leu Asp Ser Asp Gly Ser Phe Phe Leu Tyr Ser Lys Leu
            260                 265                 270

Thr Val Asp Lys Ser Arg Trp Gln Gln Gly Asn Val Phe Ser Cys Ser
        275                 280                 285

Val Met His Glu Ala Leu His Asn His Tyr Thr Gln Lys Ser Leu Ser
    290                 295                 300

Leu Ser Pro Gly Lys
305

<210> SEQ ID NO 8
<211> LENGTH: 905
<212> TYPE: DNA
<213> ORGANISM: Artificial Sequence
<220> FEATURE:
<223> OTHER INFORMATION: Human TWEAK receptor fusion protein construct
<220> FEATURE:
<221> NAME/KEY: CDS
<222> LOCATION: (1)..(903)
<223> OTHER INFORMATION:

<400> SEQUENCE: 8 atg gct cgg ggc tcg ctg cgc cgg ttg ctg cgg ctc ctc gtg ctg ggg      48
Met Ala Arg Gly Ser Leu Arg Arg Leu Leu Arg Leu Leu Val Leu Gly
1               5                   10                  15 ctc tgg ctg gcg ttg ctg cgc tcc gtg gcc ggg gag caa gcg cca ggc      96
Leu Trp Leu Ala Leu Leu Arg Ser Val Ala Gly Glu Gln Ala Pro Gly
            20                  25                  30 acc gcc ccc tgc tcc cgc ggc agc tcc tgg agc gcg gac ctg gac aag     144
Thr Ala Pro Cys Ser Arg Gly Ser Ser Trp Ser Ala Asp Leu Asp Lys
        35                  40                  45 tgc atg gac tgc gcg tct tgc agg gcg cga ccg cac agc gac ttc tgc     192
Cys Met Asp Cys Ala Ser Cys Arg Ala Arg Pro His Ser Asp Phe Cys
    50                  55                  60 ctg ggc tgc gct gca gca aga tct tgt gac aaa act cac aca tgc cca     240
Leu Gly Cys Ala Ala Ala Arg Ser Cys Asp Lys Thr His Thr Cys Pro
65                  70                  75                  80 ccg tgc cca gca cct gaa gcc gag ggc gcg ccg tca gtc ttc ctc ttc     288
Pro Cys Pro Ala Pro Glu Ala Glu Gly Ala Pro Ser Val Phe Leu Phe
                85                  90                  95 ccc cca aaa ccc aag gac acc ctc atg atc tcc cgg acc cct gag gtc     336
Pro Pro Lys Pro Lys Asp Thr Leu Met Ile Ser Arg Thr Pro Glu Val
            100                 105                 110 aca tgc gtg gtg gtg gac gtg agc cac gaa gac cct gag gtc aag ttc     384
Thr Cys Val Val Val Asp Val Ser His Glu Asp Pro Glu Val Lys Phe
        115                 120                 125 aac tgg tac gtg gac ggc gtg gag gtg cat aat gcc aag aca aag ccg     432
Asn Trp Tyr Val Asp Gly Val Glu Val His Asn Ala Lys Thr Lys Pro
    130                 135                 140 cgg gag gag cag tac aac agc acg tac cgt gtg gtc agc gtc ctc acc     480
Arg Glu Glu Gln Tyr Asn Ser Thr Tyr Arg Val Val Ser Val Leu Thr
145                 150                 155                 160 gtc ctg cac cag gac tgg ctg aat ggc aag gag tac aag tgc aag gtc     528
Val Leu His Gln Asp Trp Leu Asn Gly Lys Glu Tyr Lys Cys Lys Val
                165                 170                 175 tcc aac aaa gcc ctc cca gcc ccc atc gag aaa acc atc tcc aaa gcc     576
Ser Asn Lys Ala Leu Pro Ala Pro Ile Glu Lys Thr Ile Ser Lys Ala
            180                 185                 190 aaa ggg cag ccc cga gaa cca cag gtg tac acc ctg ccc cca tcc cgg     624
Lys Gly Gln Pro Arg Glu Pro Gln Val Tyr Thr Leu Pro Pro Ser Arg
```

```
                195                 200                 205
gag gag atg acc aag aac cag gtc agc ctg acc tgc ctg gtc aaa ggc      672
Glu Glu Met Thr Lys Asn Gln Val Ser Leu Thr Cys Leu Val Lys Gly
        210                 215                 220 ttc tat ccc agc gac atc gcc gtg gag tgg gag agc aat ggg cag ccg      720
Phe Tyr Pro Ser Asp Ile Ala Val Glu Trp Glu Ser Asn Gly Gln Pro
225                 230                 235                 240 gag aac aac tac aag acc acg cct ccc gtg ctg gac tcc gac ggc tcc      768
Glu Asn Asn Tyr Lys Thr Thr Pro Pro Val Leu Asp Ser Asp Gly Ser
                245                 250                 255 ttc ttc ctc tat agc aag ctc acc gtg gac aag agc agg tgg cag cag      816
Phe Phe Leu Tyr Ser Lys Leu Thr Val Asp Lys Ser Arg Trp Gln Gln
            260                 265                 270 ggg aac gtc ttc tca tgc tcc gtg atg cat gag gct ctg cac aac cac      864
Gly Asn Val Phe Ser Cys Ser Val Met His Glu Ala Leu His Asn His
        275                 280                 285 tac acg cag aag agc ctc tcc ctg tct ccg ggt aaa tga ac               905
Tyr Thr Gln Lys Ser Leu Ser Leu Ser Pro Gly Lys
    290                 295                 300

<210> SEQ ID NO 9
<211> LENGTH: 300
<212> TYPE: PRT
<213> ORGANISM: Artificial Sequence
<220> FEATURE:
<223> OTHER INFORMATION: Human TWEAK receptor fusion protein construct

<400> SEQUENCE: 9

Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ala Ser Cys Arg Ala Arg Pro His Ser Asp Phe Cys
    50                  55                  60

Leu Gly Cys Ala Ala Ala Arg Ser Cys Asp Lys Thr His Thr Cys Pro
65                  70                  75                  80

Pro Cys Pro Ala Pro Glu Ala Glu Gly Ala Pro Ser Val Phe Leu Phe
                85                  90                  95

Pro Pro Lys Pro Lys Asp Thr Leu Met Ile Ser Arg Thr Pro Glu Val
            100                 105                 110

Thr Cys Val Val Val Asp Val Ser His Glu Asp Pro Glu Val Lys Phe
        115                 120                 125

Asn Trp Tyr Val Asp Gly Val Glu Val His Asn Ala Lys Thr Lys Pro
    130                 135                 140

Arg Glu Glu Gln Tyr Asn Ser Thr Tyr Arg Val Val Ser Val Leu Thr
145                 150                 155                 160

Val Leu His Gln Asp Trp Leu Asn Gly Lys Glu Tyr Lys Cys Lys Val
                165                 170                 175

Ser Asn Lys Ala Leu Pro Ala Pro Ile Glu Lys Thr Ile Ser Lys Ala
            180                 185                 190

Lys Gly Gln Pro Arg Glu Pro Gln Val Tyr Thr Leu Pro Pro Ser Arg
        195                 200                 205

Glu Glu Met Thr Lys Asn Gln Val Ser Leu Thr Cys Leu Val Lys Gly
    210                 215                 220

Phe Tyr Pro Ser Asp Ile Ala Val Glu Trp Glu Ser Asn Gly Gln Pro
```

```
                225                 230                 235                 240
Glu Asn Asn Tyr Lys Thr Thr Pro Pro Val Leu Asp Ser Asp Gly Ser
                245                 250                 255

Phe Phe Leu Tyr Ser Lys Leu Thr Val Asp Lys Ser Arg Trp Gln Gln
            260                 265                 270

Gly Asn Val Phe Ser Cys Ser Val Met His Glu Ala Leu His Asn His
        275                 280                 285

Tyr Thr Gln Lys Ser Leu Ser Leu Ser Pro Gly Lys
    290                 295                 300

<210> SEQ ID NO 10
<211> LENGTH: 5
<212> TYPE: PRT
<213> ORGANISM: Artificial Sequence
<220> FEATURE:
<223> OTHER INFORMATION: Linker Moiety

<400> SEQUENCE: 10

Gly Gly Gly Gly Ser
1               5

<210> SEQ ID NO 11
<211> LENGTH: 6
<212> TYPE: PRT
<213> ORGANISM: Artificial Sequence
<220> FEATURE:
<223> OTHER INFORMATION: Linker Moiety
<220> FEATURE:
<221> NAME/KEY: misc_feature
<222> LOCATION: (6)..(6)
<223> OTHER INFORMATION: Xaa is one or more repeats of GGGGS

<400> SEQUENCE: 11

Gly Gly Gly Gly Ser Xaa
1               5

<210> SEQ ID NO 12
<211> LENGTH: 12
<212> TYPE: PRT
<213> ORGANISM: Artificial sequence
<220> FEATURE:
<223> OTHER INFORMATION: Linker Moiety

<400> SEQUENCE: 12

Gly Lys Ser Ser Gly Ser Gly Ser Glu Ser Lys Ser
1               5                   10

<210> SEQ ID NO 13
<211> LENGTH: 14
<212> TYPE: PRT
<213> ORGANISM: Artificial sequence
<220> FEATURE:
<223> OTHER INFORMATION: Linker Moiety

<400> SEQUENCE: 13

Gly Ser Thr Ser Gly Ser Gly Lys Ser Ser Glu Gly Lys Gly
1               5                   10

<210> SEQ ID NO 14
<211> LENGTH: 16
<212> TYPE: PRT
<213> ORGANISM: Artificial sequence
<220> FEATURE:
<223> OTHER INFORMATION: Linker Moiety

<400> SEQUENCE: 14
```

-continued

```
Gly Ser Thr Ser Gly Ser Gly Lys Ser Ser Glu Gly Ser Gly Ser Thr
1               5                   10                  15

<210> SEQ ID NO 15
<211> LENGTH: 16
<212> TYPE: PRT
<213> ORGANISM: Artificial sequence
<220> FEATURE:
<223> OTHER INFORMATION: Linker Moiety

<400> SEQUENCE: 15

Gly Ser Thr Ser Gly Ser Gly Lys Pro Gly Ser Gly Glu Gly Ser Thr
1               5                   10                  15

<210> SEQ ID NO 16
<211> LENGTH: 14
<212> TYPE: PRT
<213> ORGANISM: Artificial sequence
<220> FEATURE:
<223> OTHER INFORMATION: Linker Moiety

<400> SEQUENCE: 16

Glu Gly Lys Ser Ser Gly Ser Gly Ser Glu Ser Lys Glu Phe
1               5                   10
```